(12) United States Patent
Kuwahara et al.

(10) Patent No.: US 9,216,302 B2
(45) Date of Patent: Dec. 22, 2015

(54) RADIOTHERAPY SYSTEM AND RADIOTHERAPY PLANNING APPARATUS

(71) Applicants: Kabushiki Kaisha Toshiba, Minato-ku (JP); Toshiba Medical Systems Corporation, Otawara-shi (JP)

(72) Inventors: Takayuki Kuwahara, Otawara (JP); Takuzo Takayama, Utsunomiya (JP)

(73) Assignees: KABUSHIKI KAISHA TOSHIBA, Minato-ku (KE); Toshiba Medical Systems Corporation, Otawara-shi (JP)

( * ) Notice: Subject to any disclaimer, the term of this patent is extended or adjusted under 35 U.S.C. 154(b) by 196 days.

(21) Appl. No.: 13/967,848

(22) Filed: Aug. 15, 2013

(65) Prior Publication Data

US 2013/0329856 A1  Dec. 12, 2013

Related U.S. Application Data

(63) Continuation of application No. PCT/JP2013/060952, filed on Apr. 11, 2013.

(30) Foreign Application Priority Data

Apr. 11, 2012 (JP) ................. 2012-090208
May 8, 2012 (JP) ................. 2012-106801

(51) Int. Cl.
- *A61N 5/10* (2006.01)
- *A61B 6/02* (2006.01)
- *A61B 6/03* (2006.01)
- *A61B 6/00* (2006.01)

(52) U.S. Cl.
CPC .............. *A61N 5/1039* (2013.01); *A61B 6/025* (2013.01); *A61B 6/032* (2013.01); *A61B 6/4014* (2013.01); *A61B 6/4241* (2013.01); *A61B 6/481* (2013.01); *A61N 5/103* (2013.01); *A61N 5/1049* (2013.01); *A61N 5/1067* (2013.01); *A61N 2005/1061* (2013.01)

(58) Field of Classification Search
CPC ..................... A61N 5/1049; A61N 2005/1061
See application file for complete search history.

(56) References Cited

U.S. PATENT DOCUMENTS

| | | | |
|---|---|---|---|
| 7,460,640 B2 | 12/2008 | Kamikonya et al. | |
| 2004/0101104 A1* | 5/2004 | Avinash et al. | 378/98.12 |
| 2007/0019788 A1* | 1/2007 | Ledoux et al. | 378/88 |

(Continued)

FOREIGN PATENT DOCUMENTS

| | | |
|---|---|---|
| CN | 101031336 A | 9/2007 |
| CN | 101287984 A | 10/2008 |

(Continued)

OTHER PUBLICATIONS

International Search Report issued Jul. 16, 2013, in Patent Application No. PCT/JP2013/060952 (with English translation of Category of Cited Documents).

(Continued)

*Primary Examiner* — Hoon Song
(74) *Attorney, Agent, or Firm* — Oblon, McClelland, Maier & Neustadt, L.L.P.

(57) ABSTRACT

According to one embodiment, a radiotherapy apparatus generates counting data as a count value of photons included in a preset energy region based on an output signal from an observation detector. The radiotherapy apparatus generates medical image data based on the counting data.

22 Claims, 17 Drawing Sheets

(56) References Cited

U.S. PATENT DOCUMENTS

| | | | |
|---|---|---|---|
| 2007/0071171 A1* | 3/2007 | Hayashida et al. | 378/98 |
| 2008/0049896 A1* | 2/2008 | Kuduvalli | 378/65 |
| 2009/0092221 A1* | 4/2009 | Manabe et al. | 378/6 |
| 2009/0238334 A1* | 9/2009 | Brahme et al. | 378/41 |
| 2011/0282181 A1* | 11/2011 | Wang et al. | 600/407 |
| 2012/0014501 A1* | 1/2012 | Pelc et al. | 378/9 |

FOREIGN PATENT DOCUMENTS

| | | |
|---|---|---|
| JP | 2000-237335 | 9/2000 |
| JP | 2001-161839 | 6/2001 |
| JP | 2011-130929 A | 7/2011 |
| JP | 2011-217805 | 11/2011 |
| WO | WO 2011/107145 A1 | 9/2011 |

OTHER PUBLICATIONS

International Preliminary Report on Patentability and Written Opinion issued Oct. 23, 2014 in corresponding PCT/JP2013/060952 (English translation only).

International Search Report issued on Jul. 16, 2013, in Patent Application No. PCT/JP2013/060952 (submitting English translation only).

Combined Office Action and Search Report issued Jun. 26, 2015 in Chinese Patent Application No. 201380000339.5 (with English translation of Category of Cited Documents).

European Search Report mailed Oct. 29, 2015 for Application No. EP 13 74 7335.1-1652.

* cited by examiner

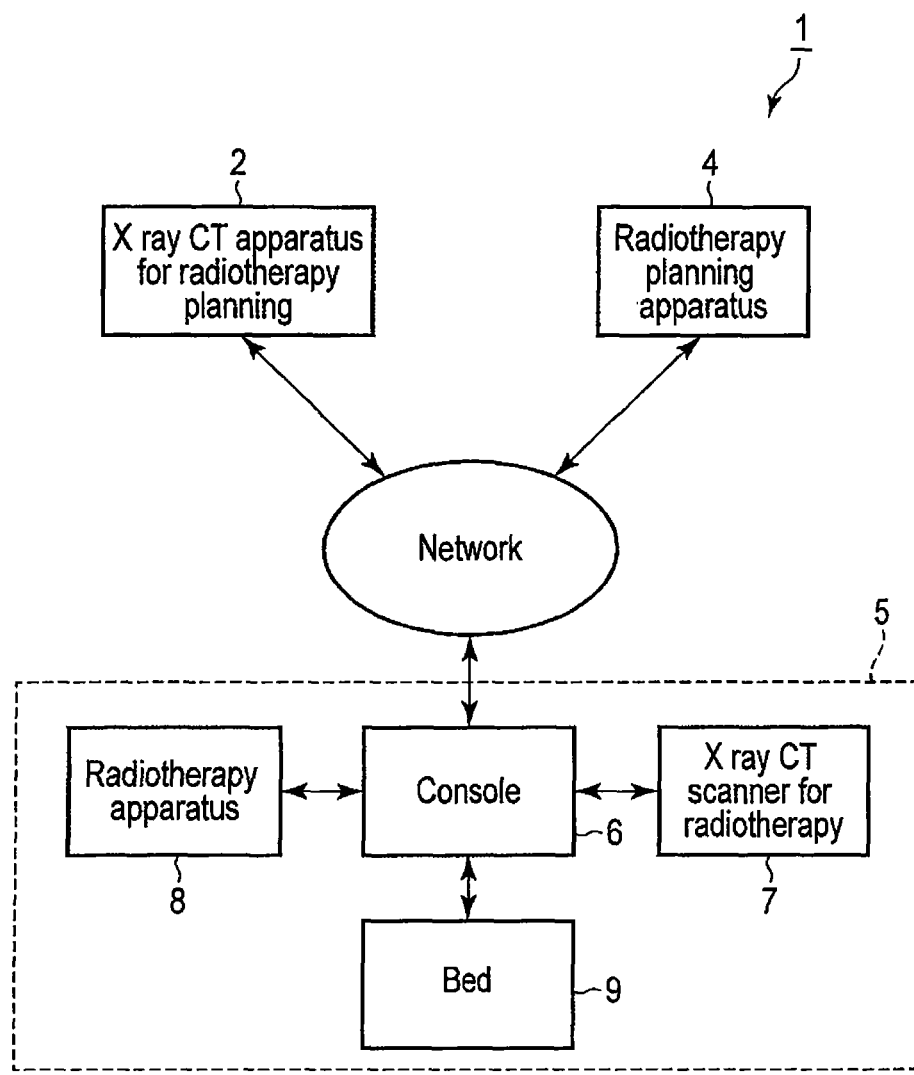
F I G. 1

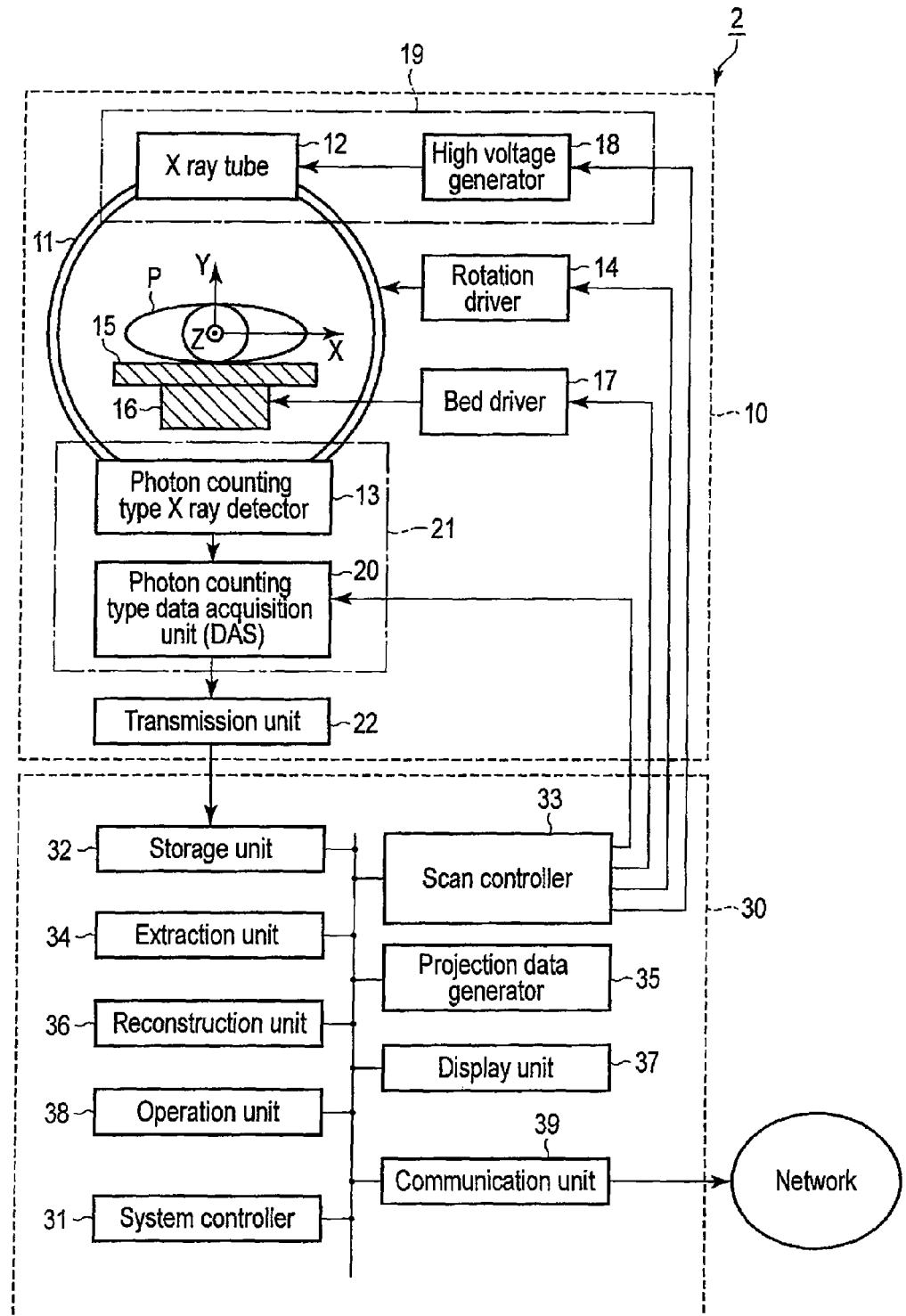
F I G. 2

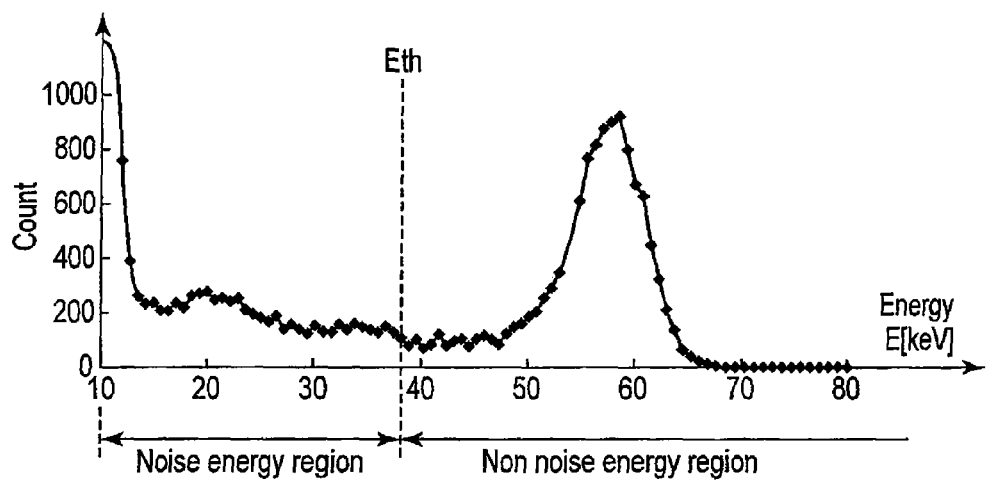
F I G. 3
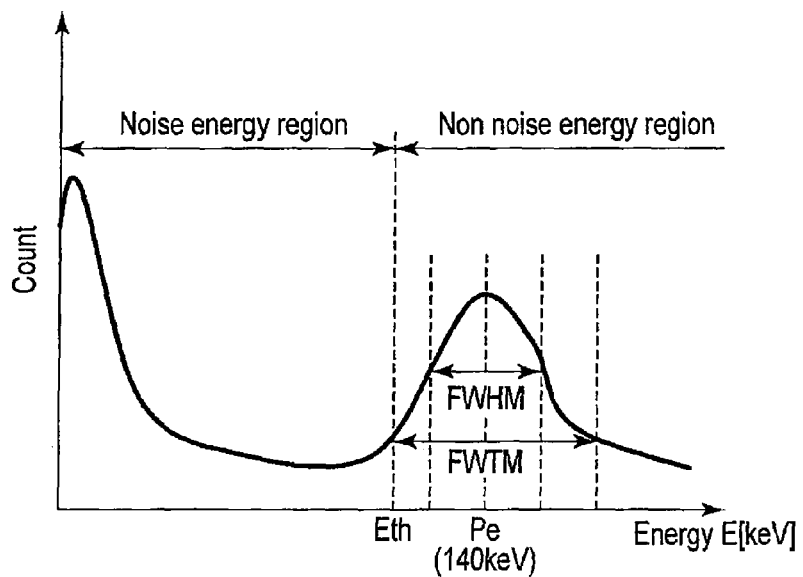
F I G. 4

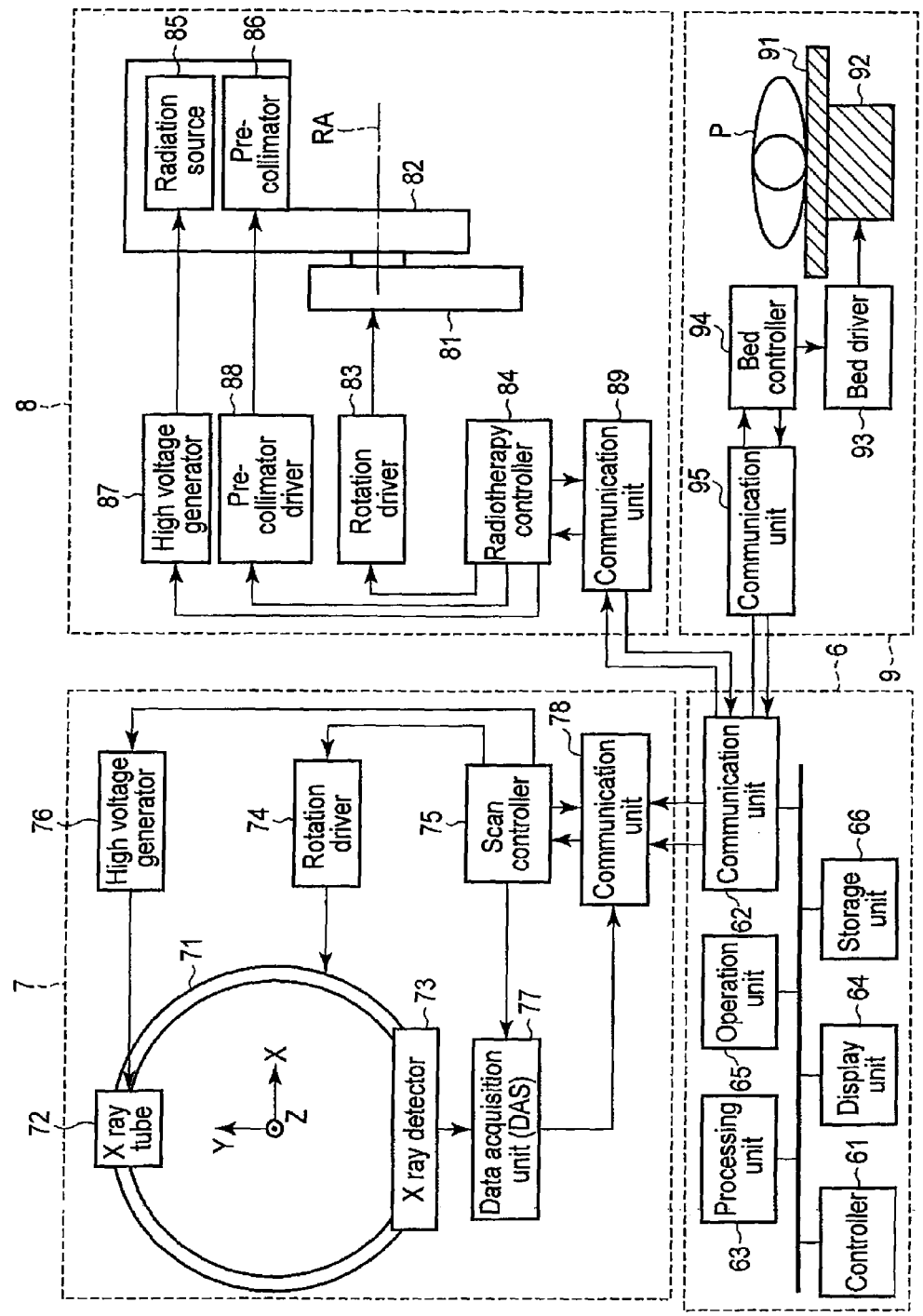
F I G. 8

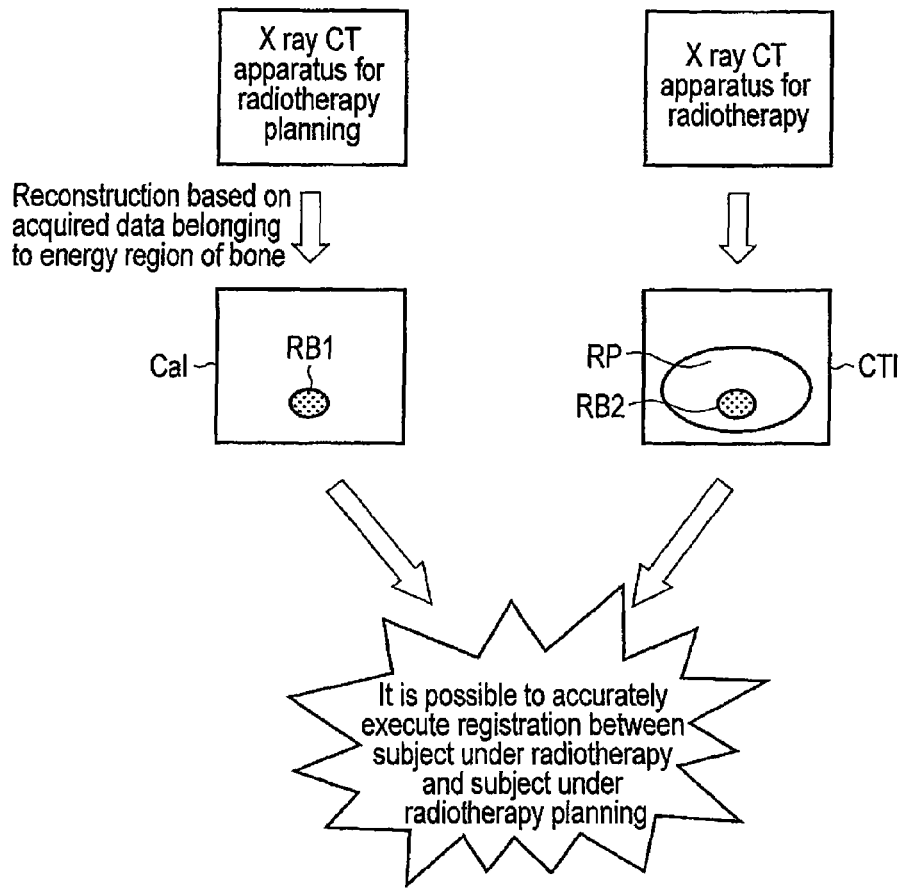
F I G. 10
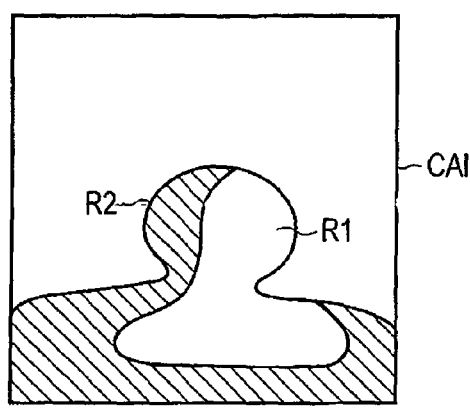
F I G. 11

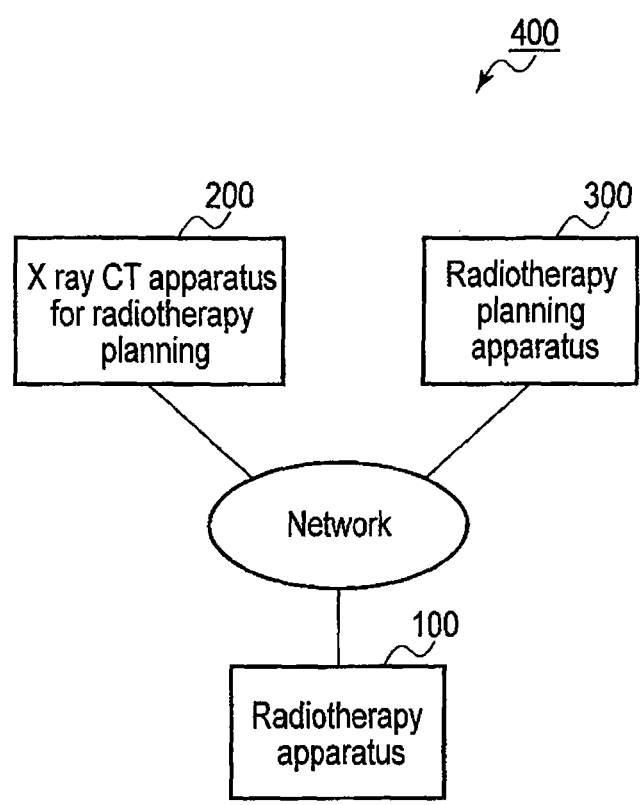
F I G. 12

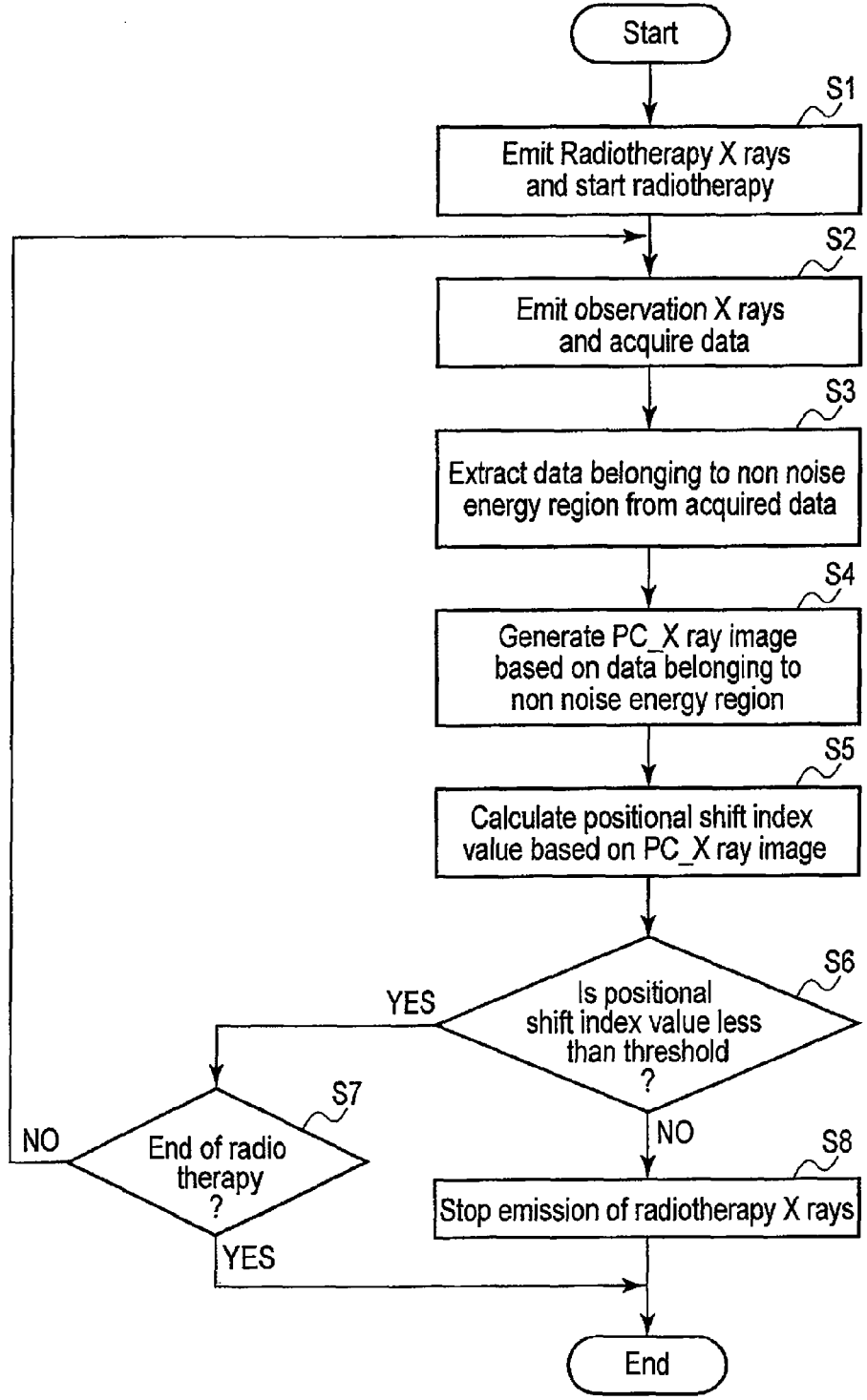
F I G. 15

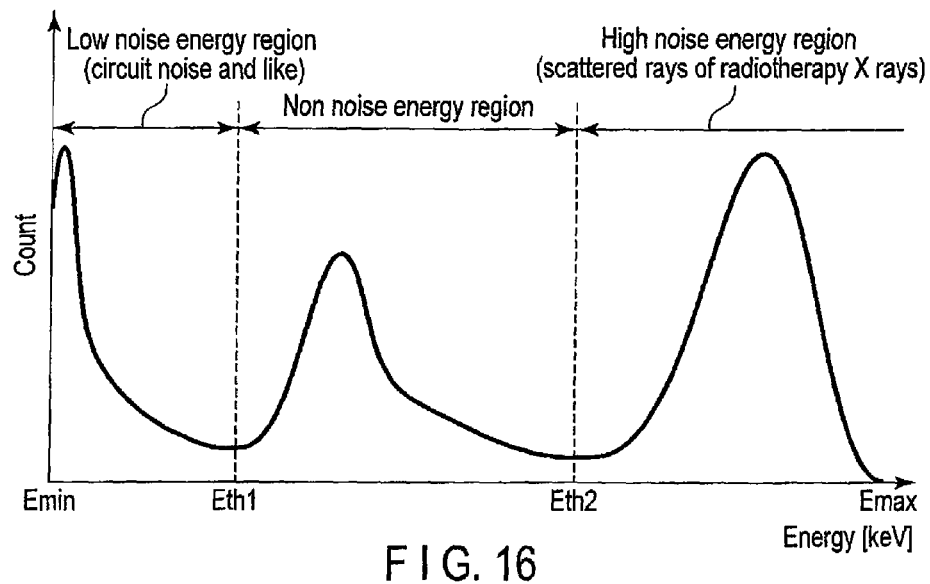
F I G. 16
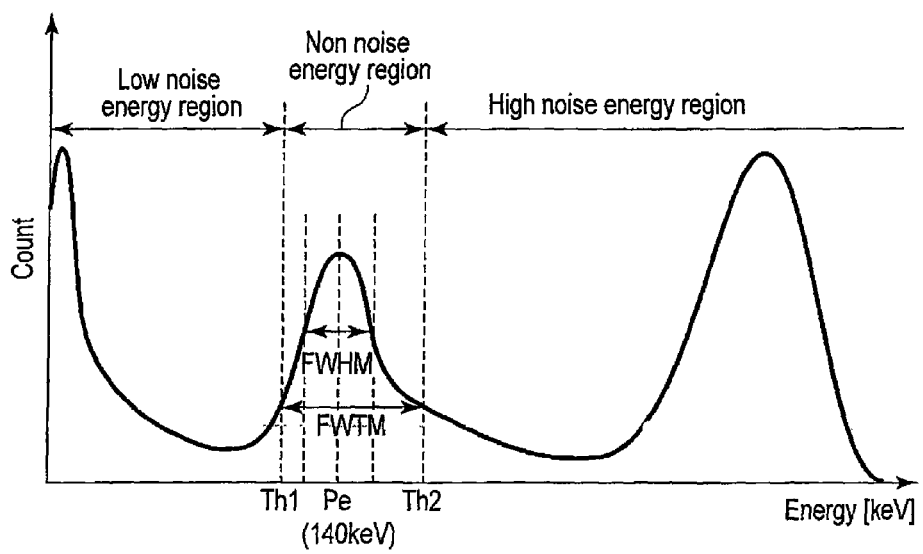
F I G. 17

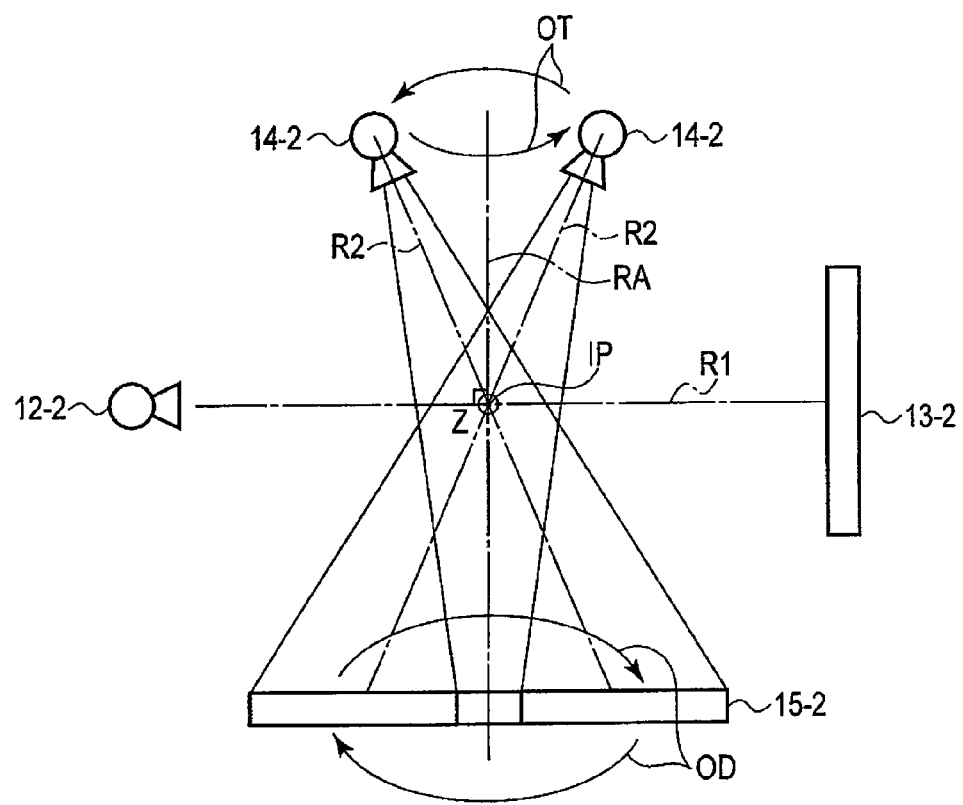
F I G. 23

RADIOTHERAPY SYSTEM AND RADIOTHERAPY PLANNING APPARATUS

CROSS REFERENCE TO RELATED APPLICATIONS

This application is a Continuation Application of PCT Application No. PCT/JP2013/060952, filed Apr. 11, 2013 and based upon and claiming the benefit of priority from Japanese Patent Applications No. 2012-090208, filed Apr. 11, 2012; and No. 2012-106801, filed May 8, 2012, the entire contents of all of which are incorporated herein by reference.

FIELD

Embodiments described herein relate generally to a radiotherapy system and a radiotherapy planning apparatus.

BACKGROUND

A radiotherapy planning apparatus uses a CT image of the inside of the subject body in radiotherapy planning. The radiotherapy planning apparatus calculates and decides radiotherapy parameters by using the CT values of the pixels of a CT image. More specifically, the radiotherapy planning apparatus calculates an electron density in the subject body from CT values, and calculates and decides radiotherapy parameters such as a radiation dose by using the electron density. The accuracy of an electron density is a very important factor in terms of guaranteeing the accuracy of radiotherapy parameters. The X-ray detection unit of an existing X-ray CT apparatus operates in the current integration mode of repeatedly integrating current pulses in the detection elements in accordance with an X-ray emission cycle. For this reason, acquired data includes noise components originating from an electronic circuit. That is, the noise components adversely affect a calculated electron density.

A radiotherapy system uses IGRT (image-guided radiotherapy). IGRT is a technique of accurately performing a radiotherapy while correcting the positional shift of a subject by using the X-ray image acquired in real time during a radiotherapy and the CT image acquired before the radiotherapy. A radiotherapy is performed over a relatively long period of time, and hence the subject moves sometimes. The motions of the subject include body motions such as the motions of the arms and legs and unavoidable motions accompanying physiological phenomena such as a respiratory motion. IGRT is equipped with an error detection technique of automatically stopping the emission of radiation upon detecting that a positional shift amount exceeds an allowable range. However, an existing imaging apparatus using X-rays operates in the current integration mode of repeatedly integrating current pulses in the detection elements in accordance with an X-ray emission cycle, and hence acquired data includes many noise components originating from an electronic circuit. The accuracy of error detection using X-ray images and CT images based on acquired data including noise components is not very high.

It is an object of an embodiment to provide a radiotherapy system and radiotherapy planning apparatus which aim at improving the accuracy of a radiotherapy.

BRIEF DESCRIPTION OF THE DRAWINGS

FIG. 1 is a block diagram showing the arrangement of a radiotherapy system according to the first embodiment.

FIG. 2 is a block diagram showing the arrangement of an X-ray CT apparatus for radiotherapy planning in FIG. 1.

FIG. 3 is a graph showing X-ray photon detection results of an X-ray detection unit in FIG. 2.

FIG. 4 is a graph for explaining a threshold decision method by an extraction unit in FIG. 2, schematically showing the energy spectrum of X-ray photons.

FIG. 8 is a block diagram showing the arrangement of a radiotherapy apparatus group in FIG. 1.

FIG. 10 is a view schematically showing a procedure for positioning processing at the time of a radiotherapy using calcium images by a radiotherapy system according to Application 1 of the first embodiment.

FIG. 11 is a view showing an example of a contrast medium image according to Application 2 of the first embodiment.

FIG. 12 is a block diagram showing a network arrangement for a radiotherapy apparatus according to the second embodiment.

FIG. 15 is a flowchart showing a typical procedure for radiotherapy automatic stop processing performed under the control of a system controller in FIG. 13.

FIG. 16 is a graph showing the count distribution of the detected energies of the events detected by a detector for an observation in FIG. 13.

FIG. 17 is a graph for explaining a method of deciding an energy threshold by an extraction unit in FIG. 13, schematically showing the count distribution of the detected energies of events.

FIG. 23 is a view for explaining the synchronous movement of an X-ray tube and detector in tomosynthesis imaging performed under the control of a gantry controller according to Application 4 of the second embodiment.

DETAILED DESCRIPTION

Figure 5:
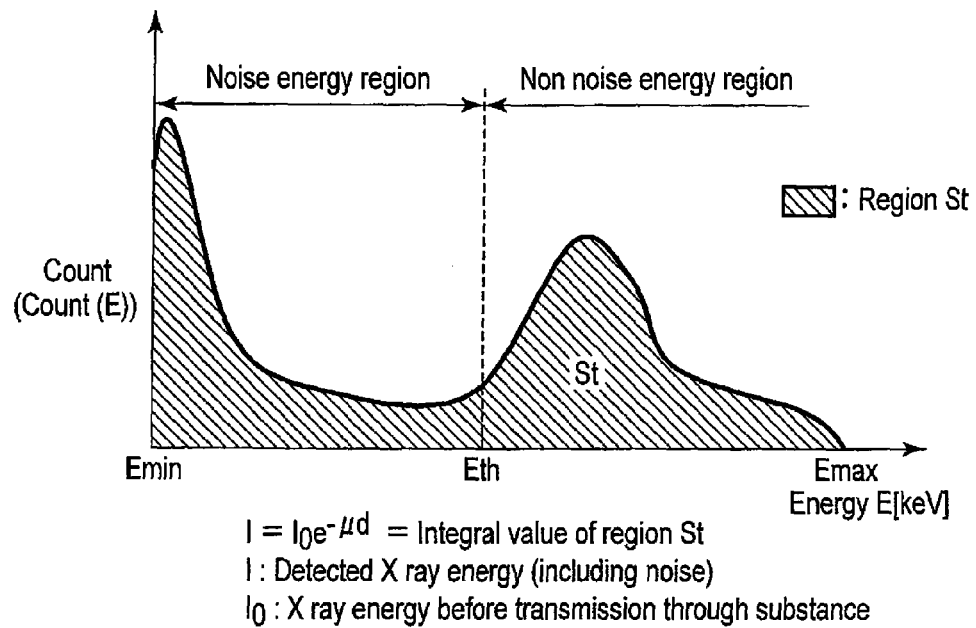
FIG. 5 is a graph for explaining projection data generation processing using the original acquired data obtained by a projection data generator in FIG. 2, showing the count value distribution of X-ray photon energies detected by the X-ray detection unit.

In general, according to one embodiment, a radiotherapy system includes a first radiation source, a first detector, a second radiation source, a counting processing unit, and an image generating unit. The first radiation source generates radiation for observation. The first detector detects radiation generated from the first radiation source and transmitted through a subject. The second radiation source generates radiation for radiotherapy. The counting processing unit generates first counting data. The first counting data includes count value of photons included in a preset energy range based on a first output signal from the first detector. The image generating unit generates first medical image data based on the first counting data.

A radiotherapy system and radiotherapy planning apparatus according to an embodiment will be described below.

(First Embodiment)

FIG. 1 is a block diagram showing the arrangement of a radiotherapy system 1 according to the first embodiment. As shown in FIG. 1, the radiotherapy system 1 includes a radiotherapy planning X-ray CT (computed tomography) apparatus 2, a radiotherapy planning apparatus 4, and a radiotherapy apparatus group 5 which are connected to each other via a network. First of all, the radiotherapy planning X-ray CT apparatus 2, the radiotherapy planning apparatus 4, and the radiotherapy apparatus group 5 will be briefly described first.

The radiotherapy planning X-ray CT apparatus 2 is an X-ray CT apparatus installed in a CT imaging room or the like in a hospital or the like. The radiotherapy planning X-ray CT apparatus 2 CT-scans a subject at a radiotherapy planning stage before a radiotherapy by using a photon counting type X-ray detection unit to acquire and calculate basic data used for radiotherapy planning. Main basic data includes, for example, CT image data expressing the spatial distribution of CT values associated with a subject.

The radiotherapy planning apparatus 4 is a computer apparatus installed in a radiotherapy control room or the like. The radiotherapy planning apparatus 4 decides radiotherapy parameters based on CT image data from the radiotherapy planning X-ray CT apparatus 2. Main radiotherapy parameters include, for example, the spatial distribution of radiation doses (to be referred to as a dose distribution hereinafter). Note that the radiotherapy planning apparatus 4 may be installed in another place other than the control room.

The radiotherapy apparatus group 5 therapeutically treats a subject with radiation in accordance with radiotherapy parameters from the radiotherapy planning apparatus 4. As shown in FIG. 1, the radiotherapy apparatus group 5 includes a console 6 as a main unit for control, a radiotherapy X-ray CT scanner 7, a radiotherapy apparatus 8, and a bed 9. The radiotherapy X-ray CT scanner 7, the radiotherapy apparatus 8, and the bed 9 are installed in a radiotherapy room. The console 6 is installed in a radiotherapy control room. The CT scanner 7 CT-scans a subject mainly immediately before a radiotherapy to generate CT image data for, for example, positioning the subject. The radiotherapy apparatus 8 irradiates the subject with radiation for a radiotherapy. More specifically, radiation is X-rays, electron beams, neutron beams, proton beams, heavy particle beams, or the like. Assume that radiation from the radiotherapy apparatus 8 in this embodiment is high-energy X-rays at the MV level. The CT scanner 7 and the radiotherapy apparatus 8 share the bed 9.

The arrangements and operations of the radiotherapy planning X-ray CT apparatus 2, radiotherapy planning apparatus 4, and radiotherapy apparatus group 5 will be described in detail next.

[Radiotherapy Planning X-Ray CT Apparatus]

FIG. 2 is a block diagram showing the arrangement of the radiotherapy planning X-ray CT apparatus 2. As shown in FIG. 2, the radiotherapy planning X-ray CT apparatus 2 includes a gantry 10 and a computer apparatus 30.

A rotating frame 11 having an annular shape is mounted on the gantry 10. The rotating frame 11 supports an X-ray tube 12 and an X-ray detector 13 so as to allow them to rotate about a subject P. The X-ray detector 13 is mounted on the rotating frame 11 so as to face the X-ray tube 12 through an FOV (field of view). The rotating frame 11 is electrically connected to a rotation driver 14. The rotation driver 14 rotates the rotating frame 11 about a rotation axis and rotates the X-ray tube 12 and the X-ray detector 13 about the subject P under the control of a scan controller 33 in the computer apparatus 30.

Note that the Z-axis is defined as the rotation axis of the rotating frame 11. The Y-axis is defined as an axis connecting the X-ray focus of the X-ray tube 12 and the center of the X-ray detection surface of the X-ray detector 13. The Y-axis is perpendicular to the Z-axis. The X-axis is defined as an axis perpendicular to the Y- and Z-axes. In this manner, the XYZ orthogonal coordinate system forms a rotating coordinate system which rotates with the rotation of the X-ray tube 12.

The subject P is placed on a top 15. The top 15 is supported by a top support mechanism 16 so as to be movable along the Z-axis. A bed driver 17 generates power for driving the top support mechanism 16 under the control of the scan controller 33. The top support mechanism 16 moves the top 15 with the generated power.

The X-ray tube 12 is electrically connected to a high voltage generator 18 via a slip ring mechanism (not shown). The X-ray tube 12 receives a high voltage from the high voltage generator 18, and generates an X-ray beam limited to a solid angle corresponding to the filter (not shown) mounted on the X-ray tube 12. X-rays may be a fan beam or cone beam. An X-ray beam includes a plurality of X-ray photons. For a concrete description of this embodiment, assume that an X-ray beam is a cone beam. The high voltage generator 18 applies a high voltage to the X-ray tube 12 under the control of the scan controller 33. This generates X-rays having an energy at the keV level. Note that the X-ray tube 12 and the high voltage generator 18 constitute an X-ray generator 19. The X-ray generator 19 generates X-ray photons under the control of the scan controller 33.

The X-ray detector 13 is a photon counting type X-ray detector. The X-ray detector 13 is connected to a photon counting type data acquisition unit (DAS: data acquisition system) 20. The X-ray detector 13 and the data acquisition unit 20 constitute an X-ray detection unit 21.

The arrangement and operation of the X-ray detection unit 21 will be described in detail below.

The X-ray detector 13 has a plurality of detection elements arrayed in the channel direction and the row direction. The channel direction is defined as a direction along an arc centered on the X-ray focus. The row direction is defined as a direction along a rotation axis Z. Each detection element detects X-ray photons from the X-ray tube 12 and generates the number of electrical pulses corresponding to the detected X-ray photon energy. As each detection element to be used, an element having physical properties suitable for the photon counting mode may be selected as needed. The X-ray detector 13 may be a semiconductor detector or scintillator type detector.

When using a semiconductor detector, each detection element is formed from a semiconductor diode. When X-ray photons enter the semiconductor diode, the semiconductor diode generates electron-hole pairs. The number of electron-hole pairs generated by the incidence of one X-ray photon is physically proportional to the energy of the input X-ray photon. The electrons and holes in the semiconductor diode are swept to the electrode by the high electric field between detection elements, thereby generating a current pulse.

When using a scintillator type detector, each detection element is formed from a combination of a scintillator and a semiconductor element (or photomultiplier tube). When X-ray photons enter the scintillator, the scintillator generates photons. The number of photons generated by the incidence of one X-ray photon is proportional to the energy of the incident X-ray photon. The semiconductor element (or photomultiplier tube) amplifies and converts the photons generated by the scintillator into current pulses.

The data acquisition unit 20 generates data indicating the energy and detection position of an X-ray photon based on a current pulse from the X-ray detector 13 under the control of the scan controller 33. More specifically, the data acquisition unit 20 includes an integration circuit and a discriminator. The integration circuit integrates current pulses from the detection elements of the X-ray detector 13 over a very short period corresponding to the incident interval of X-ray photons. The discriminator discriminates the crest value of an electrical pulse from the integration circuit. An electrical pulse from the integration circuit ideally has a crest value corresponding to the energy of a corresponding event. An event ideally includes only the incidence of a primary X-ray photon, but actually includes a pseudo-event other than the incidence of a primary X-ray photon, e.g., circuit noise or scattered X-ray photons. The data acquisition unit 20 includes a storage device which temporarily stores an energy value for each event in association with a detection position identifier. Each detection position identifier includes a view number and detection element coordinates. The detection element coordinates include a channel number and a column number. Data indicating an energy value and a detection position identifier for each event will be referred to as acquired data. A transmission unit 22 mounted on the gantry 10 transmits the acquired data to the computer apparatus 30.

In this manner, the photon counting type X-ray detection unit 21 can individually measure the energy and detection position (incident position) of an X-ray photon entering the X-ray detector 13. In photon counting, if the counting efficiency of X-ray photons is high, pileup occurs. That is, while one X-ray photon is measured, another X-ray photon enters the X-ray detector 13, resulting in difficulty in energy measurement. In order to reduce this pileup, it is preferable to set the counting efficiency to about a count of 106.

The computer apparatus 30 includes a system controller 31 as a main unit, a storage unit 32, a scan controller 33, an extraction unit 34, a projection data generator 35, a reconstruction unit 36, a display unit 37, an operation unit 38, and a communication unit 39.

The storage unit 32 stores various types of data. For example, the storage unit 32 stores the acquired data transmitted from the gantry 10 and the CT image data generated by the reconstruction unit 36.

The scan controller 33 synchronously controls the high voltage generator 18, the rotation driver 14, and the data acquisition unit 20 to execute a CT scan. More specifically, the scan controller 33 controls the rotation driver 14 to rotate the rotating frame 11 at a constant angular velocity. The scan controller 33 controls the high voltage generator 18 to generate X-rays having a predetermined intensity from the X-ray tube 12. The scan controller 33 also controls the data acquisition unit 20 to acquire acquired data in synchronism with an X-ray emission cycle.

The extraction unit 34 extracts the acquired data associated with X-ray photons belonging to a specific energy region. The projection data generator 35 generates projection data as input data for image reconstruction processing based on acquired data. The reconstruction unit 36 reconstructs CT image data indicating the spatial distribution of CT values in an imaging region of a subject based on projection data. The display unit 37 displays a CT image on the display device. Strictly, the display unit 37 displays a rendering image of the CT image. An image processing unit or the like (not shown) executes rendering. As a display unit, for example, a CRT display, liquid crystal display, organic EL display, plasma display, or the like can be used as needed. The operation unit 38 receives various types of commands and information inputs from the user via the input device. As an input device, a keyboard, mouse, switches, or the like can be used. The communication unit 39 transmits and receives various types of data between itself and the radiotherapy planning apparatus 4 or the radiotherapy apparatus group 5 via a network. For example, the communication unit 39 transmits CT image data to the radiotherapy planning apparatus 4 or the radiotherapy apparatus group 5 via the network.

The radiotherapy planning X-ray CT apparatus 2 according to this embodiment extracts the acquired data associated with a specific energy region from the acquired data acquired by the photon counting type X-ray detection unit 21, and generates CT image data based on the extracted acquired data. An imaging region of a subject is set to include a disease region or disease candidate region. Data extraction processing, projection data generation processing, and image reconstruction processing by the radiotherapy planning X-ray CT apparatus 2 will be described in detail below.

The data extraction processing executed by the extraction unit 34 will be described first. The extraction unit 34 extracts acquired data belonging to a preset specific energy region from the acquired data stored in the storage unit 32. The specific energy region is, for example, an energy region belonging to an event originating from circuit noise, scattered X-rays, or the like.

FIG. 3 is a graph showing the X-ray photon detection result obtained by the X-ray detection unit 21. Referring to the graph of FIG. 3, the ordinate defines a count, and the abscissa defines a photon energy [keV]. The numeral values in FIG. 3 are calculation results obtained by using a CdTe type detector as an X-ray detector and monochrome X-ray energy photons as X-rays. As shown in FIG. 3, noise components irrelevant to primary X-rays exist in a low-energy region less than 40 keV. A low-energy region will be referred to as a noise energy region hereinafter, and an energy region other than the noise energy region will be referred to as non-noise energy region hereinafter. The non-noise energy region is an energy region to which primary X-rays belong. More specifically, noise components originate from scattered X-rays, circuit noise from the X-ray detection unit, and the like. That is, acquired data is mixed with data associated with events originating from scattered X-rays other than primary X-rays, circuit noise, and the like. Circuit noise, in particular, is mixed in large amount with a low-energy region with about 10 keV. The acquired data associated with X-ray photons belonging to the non-noise energy region will be referred to as non-noise acquired data hereinafter.

As described above, the extraction unit 34 extracts the acquired data associated with primary X-rays from acquired data from the X-ray detection unit 21 by using a preset threshold Eth. The threshold Eth is set to an energy value which allows to discriminate noise energy from non-noise energy. The proper threshold Eth is decided based on the energy resolution of the X-ray detector 13, the flux of incident X-rays, and the energy distribution of the incident X-rays. An energy resolution corresponds to the energy required to generate electron-hole pairs in a semiconductor diode when using a semiconductor detector. When using a scintillator type detector, the energy resolution corresponds to the energy required to generate photons in the scintillator. As an energy resolution, a value measured in advance before a scan may be used. The flux of incident X-rays and an energy distribution are measured by making the X-ray detection unit 21 execute photon counting while no subject such as the subject P is placed between the X-ray tube 12 and the X-ray detector 13. The extraction unit 34 calculates a peak energy and a window band based on the energy resolution of the X-ray detector 13, the flux of incident X-rays, and the energy distribution of the incident X-rays. The extraction unit 34 decides the threshold Eth based on the peak energy and window band.

FIG. 4 is a graph for explaining a threshold decision method by the extraction unit 34, schematically showing the energy spectrum of X-ray photons. Referring to FIG. 4, the vertical axis of an energy spectrum is defined by a count, and the horizontal axis is defined by the photon energy [keV] of X-ray photons. This apparatus calculates the peak energy of incident X-rays based on the flux of the incident X-rays and the energy distribution of the incident X-rays. Assume that the peak energy of incident X-rays in FIG. 4 is 140 keV. A window band has its center at a peak energy and an energy width corresponding to an energy resolution. The energy width of the window band is set to a width corresponding to an energy resolution such as FWHM (full width at half maximum) or FWTM (full width at tenth maximum). The energy width of the window band is not limited to FWHM or FWTM and can be set to an arbitrary value corresponding to an energy resolution. Note that as the energy resolution increases, the energy width of the window band preferably decreases. When a window band is decided, the extraction unit 34 sets the threshold Eth to an energy value corresponding to the window band. For example, the threshold Eth is preferably set to the lower limit of the window band. Note that the threshold Eth may be set to an arbitrary value designated by the user via the operation unit 38.

Projection data generation processing by the projection data generator 35 and image reconstruction processing by the reconstruction unit 36 will be described next. The projection data generator 35 generates projection data as input data for image reconstruction processing based on acquired data. The original data of projection data may be either the original acquired data acquired by the X-ray detection unit 21 or the non-noise acquired data extracted by the extraction unit 34.

FIG. 5 is a graph for explaining projection data generation processing using original acquired data, showing the count value distribution of the energies of X-ray photons detected by the X-ray detection unit 21. As shown in FIG. 5, photon energies are distributed between a lower limit Emin and an upper limit Emax. An energy region less than the threshold Eth on the energy spectrum is a noise energy region originating from noise components. An energy region more than the threshold Eth is a non-noise energy region originating from primary X-rays. A Count is expressed as a function of a photon energy E.

As is known well, an energy I of X-rays detected by each detection element is expressed by $I=I_0 e^{-\mu d}$. Reference symbol I denotes the energy integration of the detected X-ray photons. That is, the energy I is the integration of Count(E) over the interval (region St in FIG. 5) from the lower limit Emin to the upper limit Emax. Reference symbol $I_0$ denotes the energy of X-rays before passing through a subject; d, the length of an X-ray path; and μ, the sum of attenuation coefficients of all substances on the X-ray path. In CT image reconstruction, $\ln(I/I_0)$ represents projection. A projection data set is defined as a data set with the projections $\ln(I/I_0)$ for the respective detection elements being arrayed in accordance with channel numbers and column numbers.

The following is an example of procedures for projection data generation processing and image reconstruction processing. First of all, the projection data generator 35 divides events according to the respective views in accordance with the detection position identifiers included in acquired data. The projection data generator 35 then calculates the projections $\ln(I/I_0)$ for the respective detection elements in accordance with the energy values of the respective events and detection position coordinates (i.e., detection elements). This generates a plurality of projection data sets associated with a plurality of views. Note that the apparatus may perform various types of corrections for acquired data. The reconstruction unit 36 reconstructs CT image data (volume data) associated with an imaging region of a subject based on projection data sets corresponding to the number of views necessary for image reconstruction. The apparatus may use, as a cone beam image reconstruction algorithm, an existing image reconstruction algorithm such as an analytical image reconstruction method, e.g., an FBP (filtered back projection) method, or sequential approximate image reconstruction, e.g., ML-EM (maximum likelihood expectation maximization) or OS-EM (ordered subset expectation maximization).

A CT image represents the three-dimensional spatial distribution of attenuation coefficients μ in an imaging region of a subject. CT values are assigned to the respective pixels constituting a CT image. A CT value is an index representing the attenuation coefficient of a substance by a relative value from the attenuation coefficient of a reference substance such as water, and is expressed as CT value=$[(\mu-\mu_0)/\mu_0] \times K$, where $\mu_0$ is the attenuation coefficient of the reference substance, and K is a constant. As shown in FIG. 5, original acquired data includes a noise energy region originating from circuit noise and the like in addition to data associated with a non-noise energy region. Therefore, noise components are mixed with the projection data or CT values based on original acquired data. A noise component degrades the quantitativity of the CT value. A noise component is depicted in a CT image to degrade the contrast of the CT image.

The radiotherapy planning X-ray CT apparatus 2 therefore improves the quantitativity of CT values by removing the noise components distributed in a low-energy region. Projection data generation processing and reconstruction processing using non-noise acquired data including no noise component will be described below.

Figure 6:
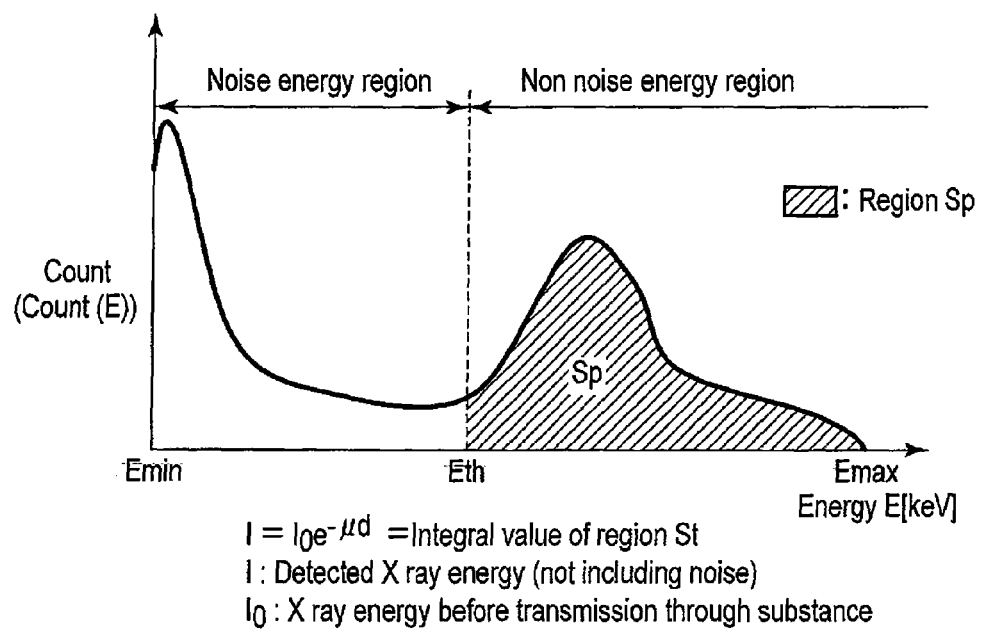
FIG. 6 is a graph for explaining projection data generation processing by the projection data generator in FIG. 2 using non-noise acquired data, showing the count value distribution of X-ray photon energies detected by the X-ray detection unit.

FIG. 6 is another graph for explaining projection data generation processing using non-noise acquired data, showing the count value distribution of energies of X-ray photons detected by the X-ray detection unit 21. As shown in FIG. 6, an energy region less than the threshold Eth on the energy spectrum is a noise energy region originating from noise components, and an energy region more than the threshold Eth is a non-noise energy region originating from primary X-rays. The extraction unit 34 has removed the data associated with the noise energy region from the non-noise acquired data. When using the non-noise acquired data, therefore, energy $I=I_0 e^{-\mu d}$ of X-rays detected by each detection element is the integration of Count(E) over the interval (a region Sp in FIG. 6) from the threshold Eth to the upper limit Emax.

The following is a projection data generation procedure using non-noise acquired data. First of all, the projection data generator 35 divides events into groups according to the respective views in accordance with the detection position numbers included in the non-noise acquired data. In the case of non-noise acquired data, events are limited to primary X-ray incidence events. The projection data generator 35 calculates the projections $\ln(I/I_0)$ for the respective detection elements in accordance with the energy values and the detection position coordinates in the respective events. This generates a plurality of projection data sets associated with a plurality of views. Note that the apparatus may perform various types of corrections for acquired data. The reconstruction unit 36 reconstructs CT image data representing the spatial distribution of CT values in an imaging region of a subject based on projection data sets corresponding to the number of views necessary for image reconstruction.

As shown in FIG. 6, non-noise acquired data includes no non-noise energy region originating from circuit noise and the like. Therefore, the CT values based on non-noise acquired data include no noise component, and exhibit higher quantitativity than the CT values based on original acquired data. Accordingly, the CT image based on the non-noise acquired data does not include much noise, and exhibits higher contrast than the CT image based on the original acquired data. Since it is possible to obtain the same image quality as that in the integration mode with a dose about 1/10 of that required in the integration mode, this embodiment can reduce the exposure dose of a subject as compared with that in the integration mode.

The communication unit 39 transmits CT image data to the radiotherapy planning apparatus 4 via a network. The CT image generated by the radiotherapy planning X-ray CT apparatus 2 will be referred to as a radiotherapy planning CT image hereinafter.

According to the above description, acquired data has a format (list mode) associating an energy value for each event with a detection position identifier. In this embodiment, however, acquired data may have a format (histogram mode) of the count value distribution of photon energies for the respective detection elements in the respective views. In this case, as in the list mode, the extraction unit 34 preferably extracts acquired data associated with energies belonging to a specific energy region.

[Radiotherapy Planning Apparatus]

The arrangement and operation of the radiotherapy planning apparatus 4 will be described next.

Figure 7:
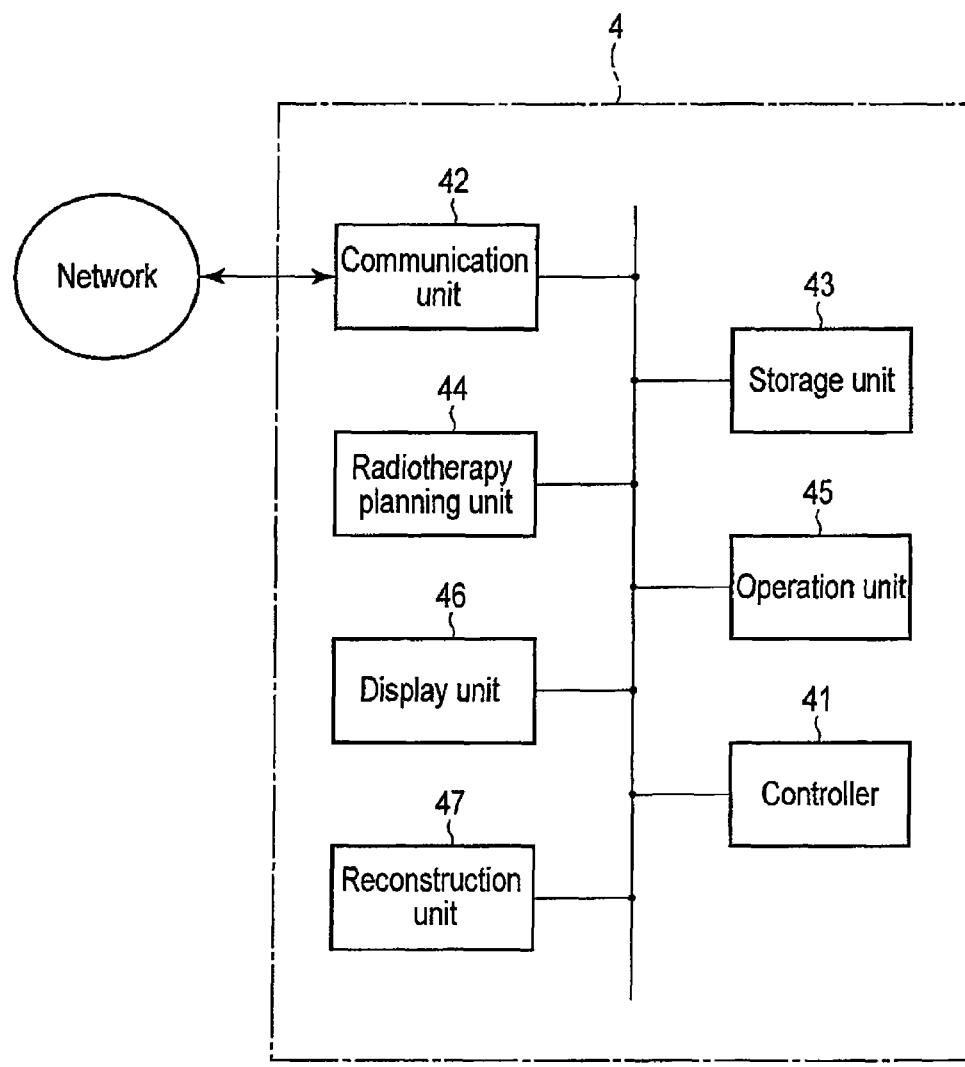
FIG. 7 is a block diagram showing the arrangement of a radiotherapy planning apparatus in FIG. 1.

FIG. 7 is a block diagram showing the arrangement of the radiotherapy planning apparatus 4. As shown in FIG. 7, the radiotherapy planning apparatus 4 includes a controller 41 as a main unit, a communication unit 42, a storage unit 43, a radiotherapy planning unit 44, an operation unit 45, a display unit 46, and a reconstruction unit 47.

The communication unit 42 transmits and receives various types of data between itself and the radiotherapy planning X-ray CT apparatus 2 and the radiotherapy apparatus group 5 via a network. For example, the communication unit 42 receives the data of a radiotherapy planning CT image, acquired data, and projection data from the radiotherapy planning X-ray CT apparatus 2 via the network. The communication unit 42 transmits the radiotherapy parameters decided by the radiotherapy planning unit 44 to the radiotherapy apparatus group 5 via the network. The storage unit 43 stores various type of data. For example, the storage unit 43 stores the data of radiotherapy planning CT images, acquired data, and projection data. The storage unit 43 also stores the radiotherapy parameters calculated by the radiotherapy planning unit 44. The radiotherapy planning unit 44 decides radiotherapy parameters according to an instruction from the user by using a radiotherapy planning CT image. The operation unit 45 accepts various types of commands and information inputs from the user via an input device. As an input device, a keyboard, mouse, switches, or the like can be used. The display unit 46 displays CT images and radiotherapy parameters. As a display unit, for example, a CRT display, liquid crystal display, organic EL display, plasma display, or the like can be used as needed. The reconstruction unit 47 reconstructs CT image (radiotherapy planning CT image) data associated with an imaging region of a subject based on projection data sets corresponding to the number of views necessary for image reconstruction which are stored in the storage unit 43.

The radiotherapy planning apparatus 4 according to this embodiment decides radiotherapy parameters by using the CT image which is transmitted from the radiotherapy planning X-ray CT apparatus 2 and to which CT values with high quantitativity are assigned. In general, radiotherapy parameters are classified into parameters for a two-dimensional radiotherapy plan using two-dimensional images from the X-ray diagnostic apparatus and parameters for a three-dimensional radiotherapy plan using three-dimensional images (volume data) from the X-ray CT apparatus. Assume that a radiotherapy plan according to this embodiment is a three-dimensional radiotherapy plan using radiotherapy planning CT images (volume data) from the radiotherapy planning X-ray CT apparatus 2.

Radiotherapy parameters include, for example, a target volume dose distribution, and irradiation conditions. Various types of target volumes include a GTV (gross tumor volume), CTV (clinical target volume), and PTV (planning target volume). Typically, the user sets these target volumes. The user observes the radiotherapy planning CT image displayed on the display unit 46 and decides various types of target volumes by synthetically determining the observation result or various types of examination results. Strictly, the display unit 46 displays the rendering image based on a radiotherapy planning CT image. The radiotherapy planning unit 44 preferably performs rendering processing. The user designates pixel regions of various types of target volumes via the operation unit 45. The radiotherapy planning unit 44 sets the designated pixel regions in various types of target volumes. A radiotherapy planning CT image according to this embodiment is reconstructed based on projection data from which noise such as circuit noise and scattered X-rays is removed, as described above, and hence includes no noise and has high contrast. Therefore, the user can accurately decide a target region.

When the user decides a target volume, the radiotherapy planning unit 44 decides irradiation conditions in accordance with the position and shape of the target volume, the positional relationship between the target volume and a risk organ, and the like. Irradiation conditions include the radiation quality, irradiation angle, and irradiation field of radiotherapy radiation.

The radiotherapy planning unit 44 calculates a dose distribution based on a radiotherapy planning CT image. More specifically, first of all, the radiotherapy planning unit 44 calculates an electron density spatial distribution by using the radiotherapy planning CT image. The radiotherapy planning unit 44 calculates an electron density based on the CT value of each pixel of the radiotherapy planning CT image.

As described above, a CT value is defined by $[(\mu-\mu_0)/\mu_0] \times K$ based on the attenuation coefficient $\mu$. An electron density is a major factor that decides the attenuation coefficient $\mu$ of a substance. For example, the radiotherapy planning unit 44 calculates the attenuation coefficient $\mu$ based on the CT value of each pixel of the radiotherapy planning CT image, and calculates an electron density based on the attenuation coefficients $\mu$. As described above, the CT values of a radiotherapy planning CT image according to this embodiment exhibit high quantitativity. For this reason, CT values according to this embodiment allow to calculate an electron density more accurately than CT values based on the X-ray detector in the integration mode.

Upon calculating an electron density spatial distribution, the radiotherapy planning unit 44 calculates a dose distribution at the time of a radiotherapy by using the calculated electron density spatial distribution. As a dose distribution calculation algorithm, for example, the Monte Carlo method is known. The Monte Carlo method is a technique of probabilistically simulating the behaviors of electrons and photons on a radiation path in consideration of various types of physical phenomena. The radiotherapy planning unit 44 calculates a dose distribution by simulating the behavior of each radiation photon on a radiation path by using the Monte Carlo method. This makes it possible to accurately simulate the absorbed dose of each tissue associated with X-rays at the MV level for a radiotherapy. Note that a dose distribution calculation algorithm which can be applied to this embodiment is not limited to only the Monte Carlo method, and any existing method such as a convolution method or superposition method can be applied.

Electron density changes depending on anatomical regions due to differences in constituent substances. In addition, electron density changes even in the same anatomical region due to differences in compositions. The radiotherapy planning unit 44 calculates a proper dose distribution in accordance with the composition of an anatomical region for each patient. This makes it possible for the radiotherapy planning apparatus 4 according to this embodiment to make a detailed radiotherapy plan and implement a tailor-made radiotherapy.

As described above, this embodiment calculates and decides radiotherapy parameters by using a CT image expressing the distribution of CT values having high quantitativity, and hence improves the accuracy of radiotherapy parameters.

[Radiotherapy Apparatus Group]

The arrangement and operation of the radiotherapy apparatus group 5 will be described next.

Figure 9:
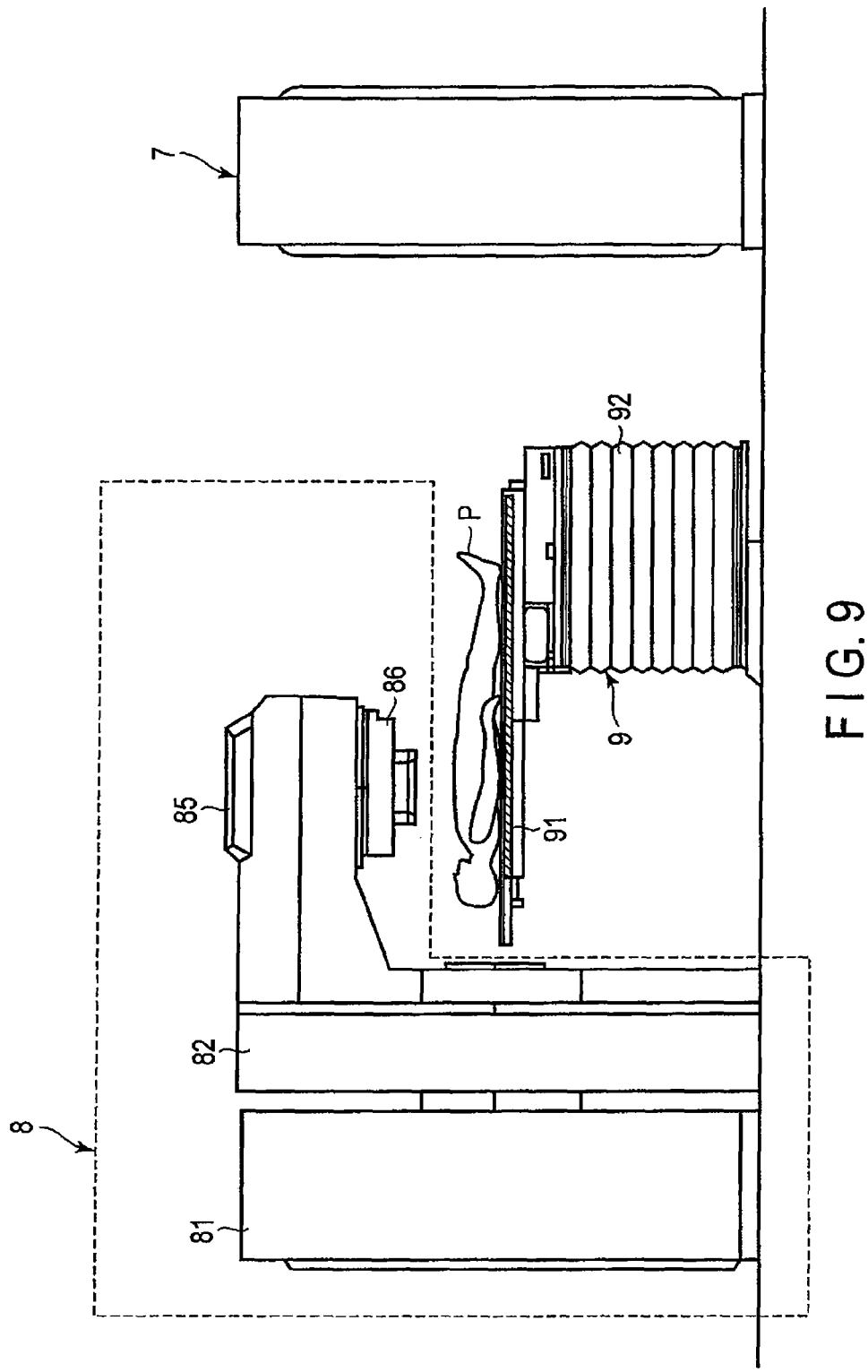
FIG. 9 is a view showing the outer appearances of an X-ray CT scanner for a radiotherapy, radiotherapy apparatus, and bed in FIG. 8.

FIG. 8 is a block diagram showing the arrangement of the radiotherapy apparatus group 5. As shown in FIG. 8, the radiotherapy apparatus group 5 includes the console 6 as a main unit, the radiotherapy X-ray CT scanner 7, the radiotherapy apparatus 8, and the bed 9. FIG. 9 is a view showing the outer appearances of the radiotherapy X-ray CT scanner 7, radiotherapy apparatus 8, and bed 9. As shown in FIG. 9, the radiotherapy X-ray CT scanner 7 and the radiotherapy apparatus 8 are discrete mechanisms.

The radiotherapy X-ray CT scanner 7 will be described first.

An annular or disk-like rotating frame 71 is mounted on the radiotherapy X-ray CT scanner 7. The rotating frame 71 supports an X-ray tube 72 and an X-ray detector 73 so as to allow them to rotate about the subject P. The X-ray detector 73 is mounted on the rotating frame 71 so as to face the X-ray tube 72 through an FOV (field of view). The rotating frame 71 is electrically connected to a rotation driver 74. The rotation driver 74 rotates the rotating frame 71 about a rotation axis under the control of a scan controller 75, and rotates the X-ray tube 72 and the X-ray detector 73 about the subject P.

Note that the Z-axis is defined as the rotation axis of the rotating frame 71. The Y-axis is defined as an axis connecting the X-ray focus of the X-ray tube 72 and the center of the X-ray detection surface of the X-ray detector 73. The Y-axis is perpendicular to the Z-axis. The X-axis is defined as an axis perpendicular to the Y- and Z-axes. In this manner, the XYZ orthogonal coordinate system forms a rotating coordinate system which rotates with the rotation of the X-ray tube 72.

The X-ray tube 72 is electrically connected to a high voltage generator 76 via a slip ring mechanism (not shown). The X-ray tube 72 receives a high voltage from the high voltage generator 76, and generates X-rays having an energy at the keV level. The high voltage generator 76 applies a high voltage to the X-ray tube 72 under the control of the scan controller 75.

The X-ray detector 73 detects the X-rays generated from the X-ray tube 72. The X-ray detector 73 includes a plurality of detection elements arrayed two-dimensionally. Each detection element detects the X-rays generated from the X-ray tube 72, and generates an electrical signal (current signal) corresponding to the intensity of the detected X-rays. Each generated electrical signal is supplied to a data acquisition unit (DAS) 77.

The data acquisition unit 77 acquires electrical signals for the respective views via the X-ray detector 73 under the control of the scan controller 75. The data acquisition unit 77 converts the acquired analog electrical signals into digital data. Digital data is called raw data. A communication unit 78 transmits the raw data to the console 6.

The scan controller 75 receives control signals from the console 6 via the communication unit 78. The scan controller 75 controls the rotation driver 74, the high voltage generator 76, and the data acquisition unit 77 in accordance with these control signals. More specifically, the scan controller 75 controls the rotation driver 74 so as to rotate the rotating frame 71 at a constant angular velocity during a CT scan. In addition, the scan controller 75 controls the high voltage generator 76 to generate X-rays from the X-ray tube 72. The scan controller 75 also controls the data acquisition unit 77 to acquire raw data for each view.

The radiotherapy apparatus 8 will be described next.

The radiotherapy apparatus 8 includes a rotation support mechanism 81. The rotation support mechanism 81 supports a support body 82 so as to allow it to rotate about a rotation axis RA. A rotation driver 83 supplies a driving signal to the rotation support mechanism 81 in accordance with an instruction from a radiotherapy controller 84. The rotation support mechanism 81 rotates the support body 82 about the rotation axis RA upon receiving the driving signal supplied from the rotation driver 83. The radiotherapy X-ray CT scanner 7 and the radiotherapy apparatus 8 are arranged such that the rotation axis RA coincides with a rotation axis Z of the rotating frame 71.

A radiation source 85 and a pre-collimator 86 are mounted on the head portion of the support body 82. The radiation source 85 generates radiation upon receiving the high voltage applied from a high voltage generator 87. The high voltage generator 87 applies a high voltage to the radiation source under the control of the radiotherapy controller 84. The pre-collimator 86 is attached to the irradiation port of the radiation source 85. The pre-collimator 86 includes a plurality of collimators for reproducing the dose distribution or irradiation field calculated by the radiotherapy planning apparatus 4. The pre-collimator 86 moves the collimators upon receiving the driving signals supplied from a pre-collimator driver 88. The pre-collimator driver 88 supplies a driving signal corresponding to a control signal from the radiotherapy controller 84 to the pre-collimator 86.

The radiotherapy controller 84 receives control signals from the console 6 via a communication unit 89. The radiotherapy controller 84 controls the rotation driver 83, the high voltage generator 87, and the pre-collimator driver 88 in accordance with these control signals. In other words, the radiotherapy controller 84 controls the rotation driver 83, the high voltage generator 87, and the pre-collimator driver 88 in accordance with the radiotherapy parameters calculated and decided by the radiotherapy planning apparatus 4. More specifically, the radiotherapy controller 84 controls the rotation driver 83 so as to rotate the support body 82 in accordance with an irradiation angle and the like of the radiotherapy parameters. The radiotherapy controller 84 controls the high voltage generator 87 to generate radiation from the radiation source 85 in accordance with a radiation quality and the like of the radiotherapy parameters. The radiotherapy controller 84 controls the pre-collimator driver 88 in accordance with the dose distribution and irradiation field of radiation.

The bed 9 will be described next.

The bed 9 includes a top 91. The top 91 is configured to allow the subject P to be placed thereon. A top support mechanism 92 supports the top 91 so as to allow it to move in the three-dimensional space defined by the x-, y-, and z-axes. A bed driver 93 supplies driving signals to the top support mechanism 92 to move the top 91 under the control of a bed controller 94. The bed controller 94 receives control signals from the console 6 via a communication unit 95. The bed controller 94 controls the bed driver 93 in accordance with these control signals.

The console 6 will be described next.

The console 6 is a computer apparatus including a controller 61 as a main unit, a communication unit 62, a processing unit 63, a display unit 64, an operation unit 65, and a storage unit 66.

The communication unit 62 transmits and receives data between itself and the radiotherapy planning X-ray CT apparatus 2, the radiotherapy planning apparatus 4, and the apparatuses 7, 8, and 9 in the radiotherapy apparatus group 5 via a network. More specifically, the communication unit 62 receives radiotherapy parameters from the radiotherapy planning apparatus 4 via the network. The communication unit 62 transmits control signals to the radiotherapy X-ray CT scanner 7, the radiotherapy apparatus 8, and the bed 9.

The processing unit 63 executes various types of data processing. For example, the processing unit 63 executes preprocessing and reconstruction processing for raw data from the radiotherapy X-ray CT scanner 7 and generates CT image data associated with the subject P immediately before the radiotherapy. The CT image based on raw data from the radiotherapy X-ray CT scanner 7 will be referred to as the radiotherapy CT image hereinafter. The processing unit 63 may generate a rendering image based on a radiotherapy CT image for display. The processing unit 63 also calculates the spatial positional shift amount between the radiotherapy planning CT image and the radiotherapy CT image to match the position of the subject at the time of a radiotherapy with the position of the subject at the time of radiotherapy planning. The positional shift amount is used for image-guided radiotherapy (to be described later).

The display unit 64 displays various types of data at the time of radiotherapy planning/radiotherapy on a display device. For example, the display unit 64 displays the rendering image based on a radiotherapy planning CT image, the rendering image based on a radiotherapy CT image, and radiotherapy parameters. As a display unit, for example, a CRT display, liquid crystal display, organic EL display, plasma display, or the like can be used as needed.

The operation unit 65 receives various types of commands and information inputs from the user via an input device. As an input device, a keyboard, mouse, switches, or the like can be used.

The storage unit 66 stores various types of data. For example, the storage unit 66 stores radiotherapy planning CT image data. The storage unit 66 also stores the radiotherapy parameters calculated by the radiotherapy planning apparatus 4.

The radiotherapy apparatus group 5 according to this embodiment executes a radiotherapy in accordance with the radiotherapy parameters decided by using the acquired data detected by the photon counting mode.

The radiotherapy apparatus group 5 can execute IGRT (image-guided radiotherapy) or DGRT (dose-guided radiotherapy). For example, in IGRT, the radiotherapy apparatus group can match the spatial position of the subject P at the time of a radiotherapy with the spatial position of the subject P at the time of capturing of a radiotherapy planning CT image by moving the top 91 and the top support mechanism 92 in accordance with the spatial positional shift amount between the radiotherapy planning CT image and the radiotherapy CT image which is calculated by the processing unit 63. The radiotherapy apparatus group 5 can also use a planning DVH (dose-value histogram) for the spatial positioning of the subject P. A planning DVH is a graph representing the relationship between the dose and the volume in a predetermined region on a CT image. The processing unit 63 calculates a planning DVH. More specifically, the processing unit 63 calculates a planning DVH in an irradiation field based on a radiotherapy CT image. It is possible to match the spatial position of the subject P at the time of a radiotherapy with the spatial position of the subject P at the time of capturing of a radiotherapy planning CT image by moving the top 91 and the top support mechanism 92 in accordance with this planning DVH.

In addition, this embodiment can calculate an accurate electron density corresponding to the composition of an analytical region. This electron density may differ with changes in the composition of an analytical region even in the same analytical region in the same subject. It is possible to detect the differences between properties in the body of the subject P at the time of capturing of a radiotherapy planning CT image and properties in the body of the subject P at the time of capturing of a radiotherapy CT image by using this characteristic. For example, the processing unit 63 calculates the differences between the radiotherapy planning CT image and the radiotherapy CT image to detect the differences in properties. If the processing unit 63 detects differences, in order to execute a radiotherapy optimal for the properties in the body of the subject at the time of the radiotherapy, the radiotherapy planning X-ray CT apparatus 2 preferably re-acquires acquired data, and the radiotherapy planning apparatus 4 preferably re-calculates radiotherapy parameters based on the re-acquired data. The radiotherapy apparatus group 5 can execute a radiotherapy suitable for the properties in the body of the subject by executing a radiotherapy in accordance with the re-calculated radiotherapy parameters. If the radiotherapy apparatus 8 is equipped with a detector which rotates together with a radiotherapy gantry, it is possible to recognize properties in the body and a dose distribution by image acquisition during a radiotherapy. This technique can therefore be applied to the detection of irradiation errors.

According to the above description, the radiotherapy X-ray CT scanner 7 and the radiotherapy apparatus 8 are discrete apparatuses. However, this embodiment is not limited to this. The radiotherapy X-ray CT scanner 7 may incorporate the radiotherapy apparatus 8. In this case, the radiotherapy apparatus 8 includes the rotating frame on which the radiation source 85 is mounted, in addition to the X-ray tube 72 and the X-ray detector 73. This allows the radiotherapy apparatus 8 to execute an X-ray scan and a radiotherapy by using the single gantry.

[Applications]

As described above, the extraction unit 34 extracts data belonging to a specific energy region from the acquired data acquired by the X-ray detection unit 21 in the photon counting mode. In the above case, a specific energy region is a noise energy region. However, this embodiment is not limited to this. The extraction unit 34 may extract acquired data belonging to an energy region to which X-ray photons which exist in the subject P and are attenuated by a preset substance to be visualized belong. The radiotherapy system 1 according to an application will be described below.

As is well known, a substance has its unique K-absorption edge. In other words, if the value of the K-absorption edge is known, the substance can be specified. The extraction unit 34 according to this application extracts acquired data associated with a specific energy region to which the K-absorption edge of each substance designated by the user for visualization from the acquired data acquired by the X-ray detection unit 21 belongs. The substances designated by the user include, for example, calcium, contrast medium, water, and other components. Other components include all components in the human body other than calcium, contrast medium, and water. A human component formed from calcium is, for example, a bone or calculus. Other components include, for example, a blood vessel, fat, muscle, brain, and soft tissue. That is, the specific energy regions are an energy region to which the K-absorption edge of calcium belongs, an energy region to which the K-absorption edge of a contrast medium belongs, an energy region to which the K-absorption edge of water belongs, and an energy region to which the K-absorption edges of other components belong. These energy regions are set in threshold ranges which do not overlap different energy regions in accordance with instructions issued by the user via the operation unit 38. These energy regions are set so as not to overlap a noise energy region. Assume that the energy region to which other K-absorption edges belong does not overlap the above noise energy region. In addition, the number of energy regions to be set is not limited to four. In this embodiment, the number of energy regions to be set may be any number more than two.

Based on the acquired data associated with the K-absorption edge of the substance designated by the user, the projection data generator 35 generates the projection data associated with the K-absorption edge of the substance. Based on the projection data associated with the K-absorption edge of the substance designated by the user, the reconstruction unit 36 reconstructs CT image data representing the spatial distribution of CT values limited to the substance. More specifically, the reconstruction unit 36 reconstructs the data of a CT image (to be referred to as a calcium image hereinafter) indicating the spatial distribution of the CT values of a contrast medium based on the projection data associated with the K-absorption edge of calcium. The reconstruction unit 36 reconstructs the data of a CT image (to be referred to as a contrast medium image hereinafter) indicating the spatial distribution of the CT values of calcium based on the projection data associated with the K-absorption edge of a contrast medium. The reconstruction unit 36 reconstructs the data of a CT image (to be referred to as a water image hereinafter) indicating the spatial distribution of the CT values of water based on the projection data associated with the K-absorption edge of water. The reconstruction unit 36 reconstructs the data of a CT image (to be referred to as an other component image hereinafter) indicating the spatial distribution of the CT values of other components based on the projection data associated with the K-absorption edges of other components. Note that each reconstructed CT image includes no noise and has high contrast because the corresponding acquired data does not belong to a noise energy region.

The radiotherapy system according to this application can reconstruct a CT image indicating the spatial distribution of the CT values limited to the substance designated by the user. The radiotherapy system 1 according to the application can apply a CT image indicating the spatial distribution of the CT values limited to the substance designated by the user to a radiotherapy plan.

Application 1:

An application of a CT image indicating the spatial distribution of the CT values limited to the substance designated by the user will be described below. Positioning using a calcium image will be described first.

FIG. 10 is a view schematically showing a procedure for positioning processing at the time of a radiotherapy using a calcium image CaI. As shown in FIG. 10, first of all, at a radiotherapy planning stage, the radiotherapy planning X-ray CT apparatus 2 generates the data of the calcium image CaI associated with the subject P and transmits the data to the console 6 of the radiotherapy apparatus group 5. The calcium image CaI dominantly includes a pixel region (to be referred to as a bone region hereinafter) RB1 associated with a bone. At a stage immediately before a radiotherapy, the radiotherapy X-ray CT scanner 7 of the radiotherapy apparatus group 5 CT-scans the same imaging region of the same subject, and the console 6 of the radiotherapy apparatus group 5 generates the data of a radiotherapy CT image CTI based on raw data from the CT scanner 7. The radiotherapy CT image CTI includes a pixel region (to be referred to as a subject region hereinafter) RP associated with the subject P. The subject region RP includes a bone region RB2. The console 6 calculates the positional shift amount between the bone region in the radiotherapy CT image CTI and the bone region in the calcium image CaI. The bone region in the radiotherapy CT image CTI is specified by existing image processing. The console 6 can match the spatial position of the subject P at the time of a radiotherapy with the spatial position of the subject P at the time of capturing of the calcium image CaI by moving the top and the support body in accordance with the calculated positional shift amount.

The radiotherapy planning X-ray CT apparatus 2 according to Application 1 generates calcium image data based on the acquired data associated with an energy region to which the K-absorption edge of calcium belongs. In principle, a calcium image depicts only a calcium region, and hence the radiotherapy planning apparatus 4 can perform positioning more accurately than the related art.

Application 2:

A radiotherapy plan using a contrast medium image will be described next.

First of all, at a radiotherapy planning stage, the radiotherapy planning X-ray CT apparatus 2 generates the contrast medium image data associated with a subject injected with a contrast medium and transmits the data to the radiotherapy planning apparatus 4. In this case, a contrast medium may be a contrast medium for angiography or a contrast medium having the property of being specifically accumulated in a human tissue, morbid region, or the like. The main raw material of a contrast medium is, for example, iodine. A contrast medium according to this embodiment, however, is not limited to that using iodine as a main raw material. The embodiment can also be applied to a contrast medium including any component with a relatively small atomic number (small mass) such as bromine or fluorine as a main raw material. Assume that a contrast medium according to this embodiment is a contrast medium having the property of being specifically accumulated in a morbid region such as a tumor.

FIG. 11 is a view showing an example of the calcium image CaI. The calcium image CaI is generated based on the acquired data associated with an energy region to which the K-absorption edge of a contrast medium belongs, and hence ideally includes only contrast medium regions R1 and R2 corresponding to the contrast medium. A contrast medium has the property of being accumulated in a morbid region. The pixel region R1 having a high contrast medium density is higher in risk than the pixel region R2 having a low contrast medium density. The radiotherapy planning apparatus 4 decides the irradiation angle of radiation based on the positions and shapes of the contrast medium regions R1 and R2 in the calcium image CaI. The radiotherapy planning apparatus 4 calculates the dose distribution associated with the decided irradiation angle by using a radiotherapy planning CT image.

Conventionally, a user such as a doctor decides a radiotherapy region by visually checking a CT image. Even with the same CT image, therefore, different users may decide different radiotherapy regions. However, the radiotherapy planning X-ray CT apparatus 2 according to Application 2 generates contrast medium image data based on the acquired data associated with an energy region to which the K-absorption edge of the contrast medium specifically accumulated in a morbid region belongs. Since the contrast medium image depicts only the contrast medium, the radiotherapy planning apparatus 4 can accurately identify a radiotherapy region as compared with the related art. In addition, this embodiment uses the photon counting mode, and the quantitativity of the resultant CT values is superior to that obtained by using the integration mode. Therefore, the embodiment exhibits the high extraction accuracy of a contrast medium region as compared with the case of extracting a contrast medium region from a CT image in the integration mode by image processing. The radiotherapy system 1 according to Application 2 can make a radiotherapy plan more accurately than the related art.

Application 3:

When comparing two or more CT images associated with the same region in the same subject, which are reconstructed by the X-ray CT apparatus in the conventional integration mode, it is difficult to compare between organs because, for example, CT values differ due to differences in the contents of the intestinal tract or the presence/absence of a contrast medium.

The extraction unit 34 according to this embodiment, however, can remove the data associated with a substance of no interest from acquired data. The extraction unit 34 can therefore remove the data associated with the contents of the intestinal tract and a contrast medium from acquired data. The reconstruction unit 36 reconstructs CT image data, from which a content region and a contrast medium region are removed, based on acquired data after removal. An image processing unit or the like (not shown) generates a difference image based on these two CT images. The difference image accurately depicts only the organ region. The user can compare between organs by observing this difference image.

Application 4:

The radiotherapy planning unit 44 can accurately perform radiotherapy planning by using a CT image indicating the spatial distribution of CT values limited to the substance designated by the user. When performing radiotherapy planning, the user designates a region to be irradiated with radiation (to be referred to as an irradiation region hereinafter) and a region with which no radiation should be irradiated (to be referred to as a non-irradiation region hereinafter) by referring to the CT image. The processing of designating an irradiation region and a non-irradiation region will be described below.

The display unit 46 of the radiotherapy planning apparatus 4 displays the CT image associated with all the energy regions. This CT image has the same characteristics as those of a CT image in the current integration mode. The user designates an irradiation region and a non-irradiation region via the operation unit 45 by observing the CT image associated with all the energy regions. The calcium component in a CT image is much higher in CT value than the surrounding tissue, and hence increases the CT value of the tissue surrounding the calcium component. For this reason, the region surrounding a calcium component generally degrades in image quality. The irradiation region and non-irradiation region designated in the CT image associated with all the energy regions which include a calcium component are low in position accuracy due to the influence of the calcium component. In order to improve the position accuracy, the display unit 46 displays the CT image associated with the substance designated by the user. For example, the display unit 46 displays a contrast medium image, water image, other component image, and the like. The display unit 46 may also display a difference image or the like based on the CT image associated with all the energy regions and a calcium image. Since the contrast medium image, water image, other component image, and difference image include no calcium component, there is no image quality degradation due to a calcium component. The user adjusts the irradiation region and the non-irradiation region while observing these images. This can further improve the position accuracy of the irradiation region and non-irradiation region.

[Effects]

As described above, the radiotherapy system 1 according to the first embodiment includes the X-ray generator 19, the X-ray detection unit 21, the extraction unit 34, the reconstruction unit 36, and the radiotherapy planning unit 44. The X-ray generator 19 generates X-ray photons. The X-ray detection unit 21 detects the X-ray photons generated from the X-ray generator 19 and transmitted through the subject P in the photon counting mode. The extraction unit 34 extracts specific acquired data associated with X-ray photons belonging to a specific energy region from the acquired data from the X-ray detection unit 21 by using a preset threshold for the specific energy region. The reconstruction unit 36 reconstructs medical image data expressing the spatial distribution of the CT values of a substance corresponding to the specific energy region based on the specific acquired data. The radiotherapy planning unit 44 decides radiotherapy parameters associated with radiotherapy of the subject P by using the medical image data.

With this arrangement, the radiotherapy system 1 according to the first embodiment can calculate CT values with higher quantitativity and hence can generate CT image data expressing the spatial distribution of the CT values with high quantitativity by using the photon counting type X-ray detection unit 21. The radiotherapy system 1 according to the first embodiment can make a more accurate radiotherapy plan because of the use of this CT image for radiotherapy planning. Improving the quantitativity of CT values can make a detailed radiotherapy plan corresponding to the tissue in the body of an individual and implement a tailor-made radiotherapy.

The first embodiment can improve the accuracy of a radiotherapy plan, and hence can improve the accuracy of a radiotherapy.

(Second Embodiment)

FIG. 12 is a block diagram showing the network arrangement of a radiotherapy apparatus 100 according to the second embodiment. As shown in FIG. 12, the radiotherapy apparatus 100 is connected to an X-ray CT (computed tomography) apparatus 200 for radiotherapy planning and a radiotherapy planning apparatus 300. The radiotherapy apparatus 100, the radiotherapy planning X-ray CT apparatus 200, and the radiotherapy planning apparatus 300 constitute a radiotherapy system 400.

The X-ray CT apparatus 200 is an X-ray CT apparatus installed in a CT imaging room in a hospital. The X-ray CT apparatus 200 CT-scans a subject at a radiotherapy planning stage, and acquires and calculates basic data to be used for radiotherapy planning. Main basic data includes, for example, CT image data expressing the spatial distribution of the CT values associated with a subject. The CT image generated by the X-ray CT apparatus 200 will be referred to as a radiotherapy planning CT image hereinafter. The radiotherapy planning CT image is volume data associated with an imaging region including a radiotherapy region.

The radiotherapy planning apparatus 300 is a computer apparatus installed in a radiotherapy control room or the like. The radiotherapy planning apparatus 300 decides radiotherapy parameters based on radiotherapy planning CT image data from the X-ray CT apparatus 200. Main radiotherapy parameters include, for example, a dose distribution, target volume, and irradiation conditions. Irradiation conditions include the quality and irradiation angle of radiotherapy radiation, irradiation energy, and radiotherapy irradiation field. Note that the radiotherapy planning apparatus 300 may be installed in a place other than a control room.

The radiotherapy apparatus 100 medically treats the subject with radiation in accordance with radiotherapy parameters from the radiotherapy planning apparatus 300. Radiation is X-rays, electron beams, neutron beams, proton beams, heavy particle beams, or the like. Assume that radiotherapy radiation in the second embodiment is high-energy X-rays at the MV level.

Figure 13:
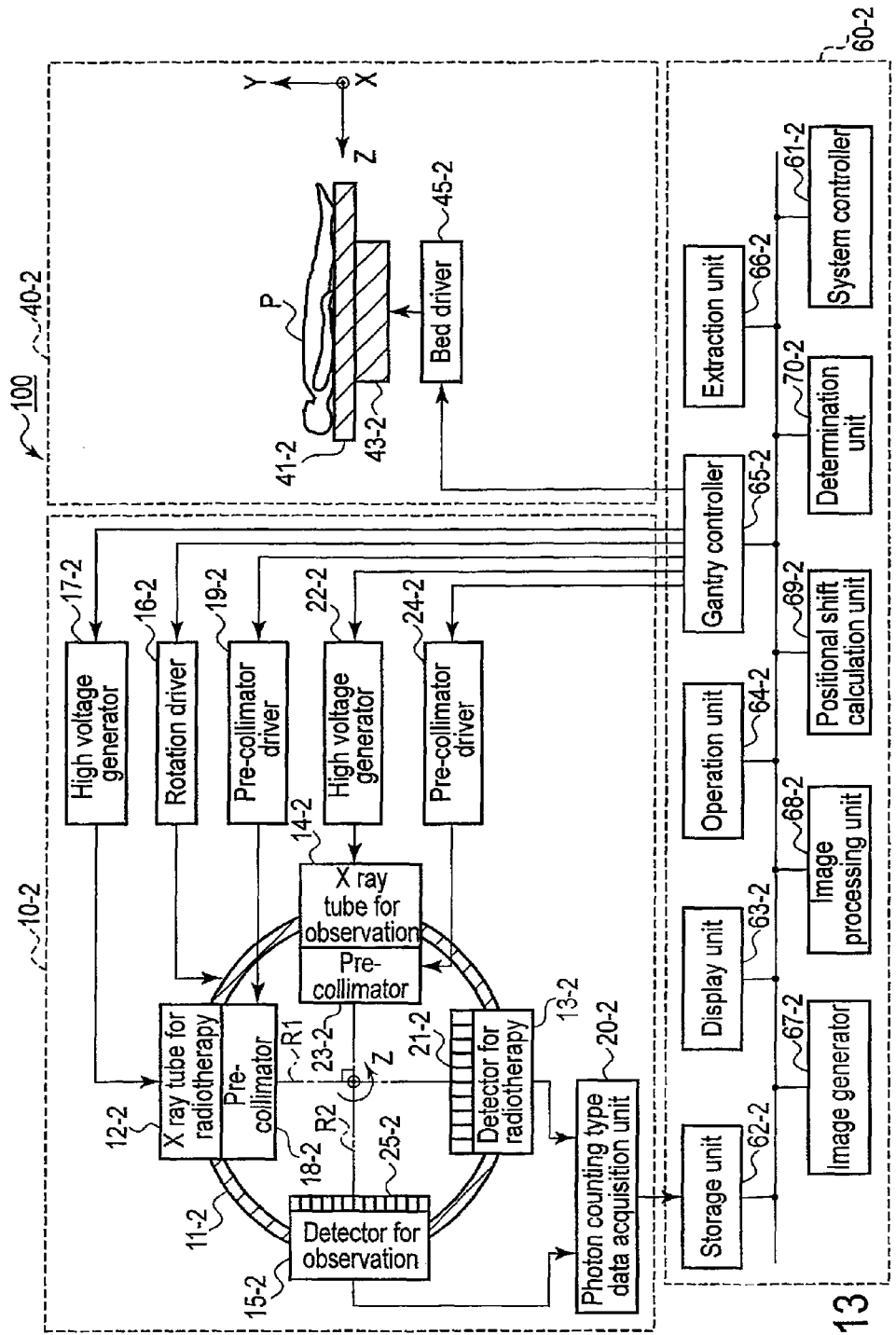
FIG. 13 is a block diagram showing the arrangement of the radiotherapy apparatus in FIG. 12.
Figure 14:
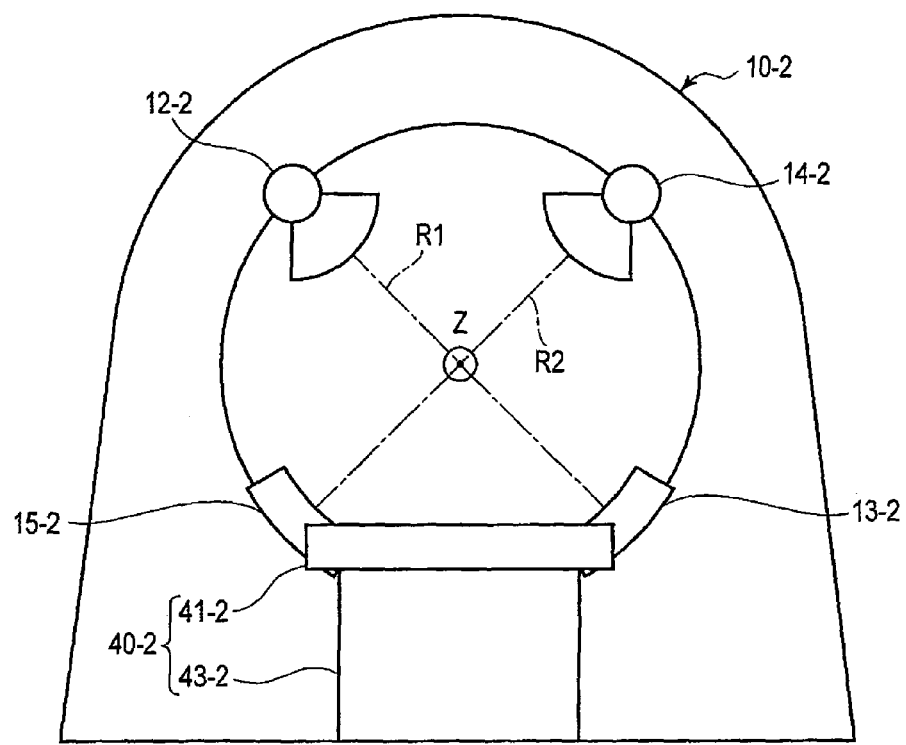
FIG. 14 is a view schematically showing the outer appearances of a radiotherapy gantry and bed in FIG. 13.

FIG. 13 is a block diagram showing the arrangement of the radiotherapy apparatus 100. As shown in FIG. 13, the radiotherapy apparatus 100 includes a radiotherapy gantry 10-2, a bed 40-2, and a console 60-2. The radiotherapy gantry 10-2 and the bed 40-2 are provided in a radiotherapy room. The console 60-2 is typically provided in a radiotherapy control room. The arrangements of the radiotherapy gantry 10-2 and bed 40-2 will be described with reference to FIGS. 13 and 14. FIG. 14 is a view schematically showing the outer appearances of the radiotherapy gantry 10-2 and bed 40-2.

As shown in FIGS. 13 and 14, the radiotherapy gantry 10-2 is equipped with two X-ray irradiation systems, namely a radiotherapy X-ray irradiation system for irradiating a radiotherapy irradiation field with X-rays for a radiotherapy and an observation X-ray irradiation system for irradiating a radiotherapy irradiation field with X-rays for an observation.

A rotating frame 11-2 is mounted on the radiotherapy gantry 10-2. An X-ray tube (to be referred to as a radiotherapy X-ray tube hereinafter) 12-2 and X-ray detector (to be referred to as a radiotherapy detector hereinafter) 13-2 of the radiotherapy X-ray irradiation system are mounted on the rotating frame 11-2, together with an X-ray tube (to be referred to as an observation X-ray tube hereinafter) 14-2 and X-ray detector (to be referred to as an observation detector hereinafter) 15-2 of the observation X-ray irradiation system.

The radiotherapy X-ray tube 12-2 and the radiotherapy detector 13-2 are mounted on the rotating frame 11-2 so as to face each other through a rotation axis Z. The observation X-ray tube 14-2 and the observation detector 15-2 are mounted on the rotating frame 11-2 so as to face each other through the rotation axis Z. The rotating frame 11-2 supports the radiotherapy X-ray tube 12-2, the radiotherapy detector 13-2, the observation X-ray tube 14-2, and the observation detector 15-2 so as to allow them to rotate about the rotation axis Z. In this case, the radiotherapy X-ray tube 12-2, the radiotherapy detector 13-2, the observation X-ray tube 14-2, and the observation detector 15-2 are mounted on the rotating frame 11-2 such that an axis R1 connecting the X-ray focus of the radiotherapy X-ray tube 12-2 to the detection surface center of the radiotherapy detector 13-2 is almost perpendicular to an axis R2 connecting the X-ray focus of the observation X-ray tube 14-2 to the detection surface center of the observation detector 15-2. Upon receiving a driving signal from a rotation driver 16-2, the rotating frame 11-2 rotates about the rotation axis Z. The rotation driver 16-2 supplies a driving signal to the rotating frame 11-2 in accordance with a control signal from a gantry controller 65-2 in a console 60-2.

Upon receiving a high voltage from a high voltage generator 17-2, the radiotherapy X-ray tube 12-2 generates high-energy X-rays at the MV (Mega Volt) level for a radiotherapy. The high voltage generator 17-2 applies a high voltage to the radiotherapy X-ray tube 12-2 in accordance with a control signal from the gantry controller 65-2. A pre-collimator 18-2 is attached to the irradiation port of the radiotherapy X-ray tube 12-2. The pre-collimator 18-2 is equipped with a multi-leaf collimator for reproducing the dose distribution and irradiation field calculated by the radiotherapy planning apparatus 300. Upon receiving the driving signal supplied from a pre-collimator driver 19-2, the pre-collimator 18-2 drives the multi-leaf collimator. The pre-collimator driver 19-2 supplies a driving signal corresponding to a control signal from the gantry controller 65-2 to the pre-collimator 19-2.

The radiotherapy detector 13-2 is a photon counting mode X-ray detector. The radiotherapy detector 13-2 includes a plurality of detection elements arrayed two-dimensionally. Each detection element detects X-ray photons from the radiotherapy X-ray tube 12-2 and generates the number of electrical pulses corresponding to the detected X-ray photon energy. As each detection element to be used, an element having physical properties suitable for the photon counting mode may be selected as needed. The radiotherapy detector 13-2 may be a semiconductor detector or scintillator type detector. The radiotherapy detector 13-2 is connected to the photon counting type data acquisition unit 20-2. Note that the rotating frame 11-2 supports the radiotherapy detector 13-2 so as to allow it to open/close. When performing no image observation with radiotherapy X-rays, the radiotherapy detector 13-2 is folded. When performing image observation with radiotherapy X-rays, the radiotherapy detector 13-2 is opened. The radiotherapy detector 13-2 is electrically connected to the data acquisition unit 20-2.

An post-collimator 21-2 is mounted on the radiotherapy detector 13-2. The post-collimator 21-2 has X-ray shielding plates assembled into a lattice form in both the channel direction and the row direction. The post-collimator 21-2 individually and optically separates the plurality of detection elements included in the radiotherapy detector 13-2 and limits the incident direction of X-ray photons to the detection elements, thereby removing scattered rays and improving the primary ray detectability of each detection element. Note that the post-collimator 21-2 may be constituted by X-ray shielding plates arrayed along only one of the channel direction and the row direction.

Upon receiving the high voltage applied from a high voltage generator 22-2, the observation X-ray tube 14-2 generates X-rays at the kV (kilo Volt) level for image observation. The high voltage generator 22-2 applies a high voltage to the observation X-ray tube 14-2 in accordance with a control signal from the gantry controller 65-2. A pre-collimator 23-2 is attached to the irradiation port of the observation X-ray tube 14-2. The pre-collimator 23-2 has a plurality of blades for limiting the solid angle of X-rays from the observation X-ray tube 14-2. Upon receiving the driving signal supplied from a pre-collimator driver 24-2, the pre-collimator 23-2 moves a plurality of blades. The pre-collimator driver 24-2 supplies a driving signal corresponding to a control signal from the gantry controller 65-2 to the pre-collimator 23-2.

The observation detector 15-2 is an X-ray detector for the photon counting mode. The observation detector 15-2 includes a plurality of detection elements arrayed two-dimensionally. Each detection element detects X-ray photons from the observation X-ray tube 14-2 and generates the number of electrical pulses corresponding to the detected X-ray photon energy. The observation detector 15-2 may be a semiconductor detector or scintillator type detector. The observation detector 15-2 is electrically connected to the data acquisition unit 20-2. A post-collimator 25-2 having almost the same structure as that of the post-collimator 21-2 is mounted on the observation X-ray tube side of the observation detector 15-2.

The radiotherapy detector 13-2 and the observation detector 15-2 share the data acquisition unit 20-2. The data acquisition unit 20-2 acquires electrical pulses from the radiotherapy detector 13-2 and the observation detector 15-2 in the photon counting mode under the control of the gantry controller 65-2, and generates acquired data based on the electrical pulses. The data acquisition unit 20-2 includes a storage device which temporarily stores an energy value for each event in association with detection element coordinates. Acquired data includes data of an energy value for each event and detection element coordinates. Note that detection element coordinates are defined by the channel number and column number of the detection element. For example, a transmission unit (not shown) mounted on the radiotherapy gantry 10-2 transmits acquired data to a console 60.

The bed 40-2 includes a top 41-2. The top 41-2 is configured to allow the subject P to be placed on it. A top support mechanism 43-2 supports the top 41-2 so as to allow it to move in the three-dimensional space defined by the x-, y-, and z-axes. A bed driver 45-2 supplies a driving signal to the top support mechanism 43-2 to move the top 41-2 in accordance with a control signal from the gantry controller 65-2.

The arrangement of the console 60-2 will be described next with reference to FIG. 13. The console 60-2 includes a system controller 61-2 as a main unit, a storage unit 62-2, a display unit 63-2, an operation unit 64-2, a gantry controller 65-2, an extraction unit 66-2, an image generator 67-2, an image processing unit 68-2, a positional shift calculation unit 69-2, and a determination unit 70-2.

The storage unit 62-2 stores acquired data from the data acquisition unit 20-2. The storage unit 62-2 also stores the medical image data generated by the image generator 67-2. The storage unit 62-2 stores the radiotherapy planning CT image data generated in advance by the radiotherapy planning X-ray CT apparatus 200 and radiotherapy parameters from the radiotherapy planning apparatus 300.

The display unit 63-2 displays various types of medical images and radiotherapy parameters on a display device. As a display device, for example, a CRT display, liquid crystal display, organic EL display, plasma display, or the like can be used as needed.

The operation unit 64-2 receives various types of commands and information inputs from the user via an input device. As an input device, a keyboard, mouse, switches, or the like can be used.

The gantry controller 65-2 synchronously controls the rotation driver 16-2, the high voltage generator 17-2, and the pre-collimator driver 19-2 to execute a radiotherapy. More specifically, the gantry controller 65-2 controls the rotation driver 16-2 to place the radiotherapy X-ray tube 12-2 at a rotational angle corresponding to an irradiation angle, controls the high voltage generator 17-2 to generate X-rays having an intensity corresponding to irradiation energy from the radiotherapy X-ray tube 12-2, and controls the pre-collimator driver 19-2 to drive the post-collimator 18-2 so as to reproduce a dose distribution and an irradiation field.

The gantry controller 65-2 can execute control for medical image capturing as well as control for a radiotherapy. Modes for medical image capturing are roughly classified into X-ray imaging modes and CT imaging modes. The X-ray imaging modes include an X-ray imaging mode using radiotherapy X-rays and an X-ray imaging mode using observation X-rays. In the X-ray imaging mode using radiotherapy X-rays, the gantry controller 65-2 controls the data acquisition unit 20-2 to generate acquired data originating from radiotherapy X-rays. In the X-ray imaging mode using observation X-rays, the gantry controller 65-2 synchronously controls the high voltage generator 22-2, the pre-collimator driver 24-2, and the data acquisition unit 20-2. More specifically, the gantry controller 65-2 controls the high voltage generator 22-2 to generate X-rays at the kV level from the observation X-ray tube 14-2, controls the pre-collimator driver 24-2 to limit observation X-rays to a predetermined solid angle, and controls the data acquisition unit 20-2 to generate acquired data originating from observation X-rays. The gantry controller 65-2 may control the rotation driver 16-2 to place the observation X-ray tube 14-2 at a predetermined rotational angle. The gantry controller 65-2 may simultaneously execute the X-ray imaging mode using radiotherapy X-rays during or before a radiotherapy. In the CT imaging mode, the gantry controller 65-2 simultaneously controls the rotation driver 16-2, the high voltage generator 22-2, and the data acquisition unit 20-2. More specifically, the gantry controller 65-2 controls the rotation driver 16-2 to rotate the observation X-ray tube 14-2 at a predetermined angular velocity, controls the high voltage generator 22-2 to periodically generate X-rays at the kV level from the observation X-ray tube 14-2, and controls the data acquisition unit 20-2 to generate acquired data for each view in synchronism with an X-ray emission cycle.

The extraction unit 66-2 extracts the acquired data associated with an energy region to which a visualization target belongs from the acquired data stored in the storage unit 62-2. An energy region is defined by a preset energy threshold. Acquired data before extraction processing will be referred to as original acquired data. If, for example, an energy region to which a visualization target belongs is an energy region (non-noise energy region) to which a component other than noise components belongs. In this case, visualization targets correspond to all substances through which X-rays pass, typically a subject. Noise components are energy components associated with events other than primary rays, e.g., circuit noise and scattered rays. That is, an energy region to which a visualization target belongs is a non-noise energy region, acquired data from which a noise component is removed is extracted. An energy region to which a visualization target belongs may be an energy region to which the K-absorption edge of a specific substance belongs. In this case, a visualization target corresponds to a specific substance of the substances included in a subject. More specifically, specific substances are classified into four types of substances, namely water, calcium, contrast medium, and others. The user can arbitrarily set a visualization target via the operation unit 64-2.

The image generator 67-2 generates medical image data associated with a visualization target based on the acquired data extracted by the extraction unit 66-2. The generated medical image originates from the one-shot X-rays emitted from the observation X-ray tube 14-2 from a single irradiation angle. In the X-ray imaging mode, the image generator 67-2 generates X-ray image data representing an X-ray transmission image limited to a visualization target based on acquired data after extraction. The X-ray image obtained by using the photon counting mode will be referred to as a PC_X-ray image hereinafter to be discriminated from the X-ray image obtained by using the current integration mode. In the CT imaging mode, the image generator 67-2 generates CT image data expressing the spatial distribution of CT values limited to a visualization target based on acquired data after extraction. The CT image obtained by using the photon counting mode will be referred to as a PC_CT image hereinafter to be discriminated from the CT image obtained by using the current integration mode. Note that input data for image generation processing is not limited to acquired data after extraction, and may be original acquired data.

The image processing unit 68-2 performs various types of image processing for a PC_X-ray image, PC_CT image, and radiotherapy planning CT image. For example, the image processing unit 68-2 performs three-dimensional image processing for a PC_CT image. Three-dimensional image processing includes pixel value projection processing, volume rendering, and MPR (Multi-Planar Reconstruction).

The positional shift calculation unit 69-2 calculates an index value (to be referred to as a positional shift index value hereinafter) associated with the body motion amount of a subject during a radiotherapy. More specifically, the positional shift calculation unit 69-2 calculates, as a positional shift index value, the spatial movement amount of a reference region included in the medical image generated by the image generator 67-2. A reference region may be any region which can be accurately extracted from a medical image. Reference regions include, for example, a pixel region (to be referred to as a contrast medium region hereinafter) corresponding to a contrast medium, a pixel region (to be referred to as a calcium region hereafter) corresponding to calcium, and a pixel region (to be referred to as a marker region hereinafter) corresponding to a marker.

The determination unit 70-2 determines whether a positional shift index value falls within a preset allowable range. If the positional shift index value falls within the allowable range, a radiotherapy continues. If the positional shift index value does not fall within the allowable range, the gantry controller 65-2 stops emitting radiotherapy X-rays.

With that, the description of the arrangement of the radiotherapy apparatus 100 is complete. According to the above description, the radiotherapy apparatus 100 according to this embodiment includes the data acquisition unit 20-2 and the extraction unit 66-2 which are functionally and structurally separated from each other. However, the embodiment is not limited to this. For example, in the radiotherapy apparatus 100, the data acquisition unit 20-2 may be equipped with the function of the extraction unit 66-2.

In this case, the data acquisition unit 20-2 and the extraction unit 66-2 will be collectively referred to as a counting processing unit. The counting processing unit in the second embodiment may be configured to obtain counting data included in a preset energy range based on electrical pulses from the radiotherapy detector 13-2 and the observation detector 15-2. This preset energy range corresponds to an energy region to which a visualization target belongs, as described above. As described above, for example, the counting processing unit according to this embodiment is configured to make the radiotherapy gantry 10-2 generate acquired data (counting data) of all events, make the console 60-2 store the acquired data of all the events, and make the console 60-2 extract the acquired data included in an energy region to which a visualization target belongs from the acquired data of all the events. The counting processing unit according to the second embodiment may take another form, in which the radiotherapy gantry 10-2 extracts electrical pulses included in an energy region to which a visualization target belongs from electrical pulses from the radiotherapy detector 13-2 and the observation detector 15-2 and generates acquired data limited to the extracted electrical pulses.

According to the above description, counting data according to this embodiment is digital data including the energy value and detection element coordinates of each event. However, the embodiment is not limited to this. For example, counting data may be digital data including the count value and detection element coordinates of each event.

For a concrete description, the counting processing unit according to this embodiment is constituted by the data acquisition unit 20-2 and the extraction unit 66-2 which are functionally and structurally separated from each other, as shown in FIG. 13.

As described above, the radiotherapy apparatus 100 includes a data acquisition system constituted by the photon counting type X-ray detectors 13-2 and 15-2 and the data acquisition unit 20-2. The radiotherapy apparatus 100 uses the medical image based on the acquired data acquired in the photon counting mode for an automatic stop function for a radiotherapy using a positional shift index value.

An example of the operation of the automatic radiotherapy stop function performed under the control of the system controller 61-2 will be described below. Note that in the following example of operation, the reference region used in the process of calculating a positional shift index value is a contrast medium region corresponding to a contrast medium combined with a medical agent having the property of being accumulated in a tissue in a radiotherapy irradiation field, e.g., a tumor. A contrast medium may be a medium including any component as a main component such as iodine, bromine, or fluorine. For a concrete description, assume that the medical agent combined with a contrast medium has the property of being accumulated in a tumor.

FIG. 15 is a flowchart showing a typical procedure for a radiotherapy performed under the control of the system controller 61-2. The user administers a contrast medium into the subject P before a radiotherapy. The contrast medium administered in the subject begins to be accumulated in a tumor as a radiotherapy target with the lapse of time. When preparation for a radiotherapy is complete, the user inputs an instruction to start a radiotherapy issued by the user via the operation unit 64-2.

As shown in FIG. 15, the system controller 61-2 causes the gantry controller 65-2 to start a radiotherapy in response to an instruction to start a radiotherapy issued by the user via the operation unit 64-2 (step S1). In step S1, the gantry controller 65-2 synchronously controls the rotation driver 16-2, the high voltage generator 17-2, and the pre-collimator driver 19-2 to execute a radiotherapy. More specifically, the gantry controller 65-2 controls the rotation driver 16-2 to place the radiotherapy X-ray tube 12-2 at a rotational angle corresponding to an irradiation angle, and controls the pre-collimator driver 19-2 to drive the multi-leaf collimator so as to reproduce a dose distribution and an irradiation field. When preparation for the emission of radiotherapy X-rays is complete, the gantry controller 65-2 controls the high voltage generator 17-2 in accordance with an irradiation energy so as to irradiate the subject P in a radiotherapy irradiation field with radiotherapy X-rays from the radiotherapy X-ray tube 12-2.

Upon starting a radiotherapy, the system controller 61-2 causes the gantry controller 65-2 to start the X-ray imaging mode to detect a positional shift (step S2). In step S2, the gantry controller 65-2 synchronously controls the high voltage generator 22-2, the pre-collimator driver 24-2, and the data acquisition unit 20-2 to obtain a PC_X-ray image. More specifically, the gantry controller 65-2 controls the pre-collimator driver 24-2 to limit radiotherapy X-rays at a predetermined solid angle. When preparation for the emission of radiotherapy X-rays is complete, the gantry controller 65-2 controls the high voltage generator 22-2 to cause the observation X-ray tube 14-2 to emit observation X-rays. Observation X-rays may be intermittently and repeatedly emitted or continuously emitted. The gantry controller 65-2 then controls the data acquisition unit 20-2 to generate acquired data originating from observation X-rays in synchronism with an X-ray emission time. The acquired data is transmitted to the console 60-2 and stored in the storage unit 62-2.

Upon executing step S2, the system controller 61-2 causes the extraction unit 66-2 to execute extraction processing (step S3). In step S3, the extraction unit 66-2 extracts data belonging to a non-noise energy region from the acquired data acquired in step S2. The extraction processing performed by the extraction unit 66-2 will be described in detail below.

FIG. 16 is a graph showing the count distribution of detected energies of events detected by the observation detector 15-2. Referring to the graph of FIG. 16, the ordinate defines a count, and the abscissa defines a photon energy [keV]. As shown in FIG. 16, the detected energies of the respective events are distributed in the range from a minimum value Emin to a maximum value Emax. A low-energy region less than an energy Eth1 includes energies originating from circuit noise from the observation detector 15-2, scattered rays of observation X-rays, and the like. A high-energy region more than an energy Eth2 includes energies of scattered rays of radiotherapy X-rays. A low-energy region less than Eth1 will be referred to as a low noise energy region. An energy region more than Eth1 and less than Eth2 will be referred to as a non-noise energy region. An energy region more than Eth2 will be referred to as a high-energy region. As described above, the data associated with circuit noise, scattered rays of observation X-rays, scattered rays of radiotherapy X-rays, and the like is mixed in the data acquired by the observation detector 15-2.

As described above, an extraction unit 34-2 extracts the acquired data associated with a non-noise energy region from the acquired data generated by the data acquisition unit 20-2 by using the preset thresholds Eth1 and Eth2. The threshold Eth1 is set to an energy value which can discriminate a low noise energy from a non-noise energy. The threshold Eth2 is set to an energy value which can discriminate a non-noise energy from a high noise energy. The thresholds Eth1 and Eth2 are properly decided based on the energy resolution of the observation detector 15-2, an incident X-ray flux, and an incident X-ray energy distribution. An energy resolution corresponds to the energy required to the generation of an electron-hole pair in the case of a semiconductor detector, and corresponds to the energy required for the generation of a photon in the case of a scintillator type detector. As an energy resolution, the value measured in advance before imaging may be used. An incident X-ray flux and an energy distribution are measured by executing photon counting using the data acquisition unit 20-2 while no subject such as the subject P is placed between the observation X-ray tube 14-2 and the observation detector 15-2. The extraction unit 66-2 then calculates a peak energy and window band based on the energy resolution of the observation detector 15-2, incident X-ray flux, and incident X-ray energy distribution. The extraction unit 66-2 decides the thresholds Eth1 and Eth2 based on the peak energy and the window band.

FIG. 17 is a graph for explaining a method of deciding an energy threshold using the extraction unit 66-2, schematically showing the energy spectrum of X-ray photons. The peak energy of observation X-rays from the observation detector 15-2 is calculated based on an incident X-ray flux and an incident X-ray energy distribution. Assume that the peak energy in FIG. 17 is 140 keV. A window band has its center at a peak energy and an energy width corresponding to an energy resolution. The energy width of the window band is set to a width corresponding to an energy resolution such as FWHM (full width at half maximum) or FWTM (full width at tenth maximum). The energy width of the window band is not limited to FWHM or FWTM and can be set to an arbitrary value corresponding to an energy resolution. Note that as the energy resolution increases, the energy width of the window band preferably decreases. When a window band is decided, the extraction unit 66-2 sets the thresholds Eth1 and Eth2 to energy values corresponding to the window band. For example, the threshold Eth1 is preferably set to the lower limit of the window band, and the threshold Eth2 is preferably set to the upper limit of the window band. Note that the thresholds Eth1 and Eth2 may be set to arbitrary values designated by the user via the operation unit 64-2.

Upon executing step S3, the system controller 61-2 causes the image generator 67-2 to perform image generation processing (step S4). In step S4, the image generator 67-2 generates PC_X-ray image data based on the acquired data extracted in step S3.

More specifically, first of all, the image generator 67-2 reads the acquired data extracted in step S3 and counts the number of events in an energy value specific manner for each detection element coordinate value (i.e., each detection element). The image generator 67-2 then executes energy integration of a count. More specifically, the image generator 67-2 integrates a count Count(E) over the interval from the threshold Eth1 to the threshold Eth2. An integral value does not include any energy originating from noise such as circuit noise, scattered rays of observation X-rays, and scattered rays of threshold X-rays, and corresponds to a detected primary X-ray intensity (photon energy×photon count). In other words, the integral value strictly corresponds to the absorption coefficient of all the substances on the X-ray path. The image generator 67-2 generates PC_X-ray image data by assigning an integral value to a pixel corresponding to each detection element. This PC_X-ray image is based on only the acquired data belonging to a non-noise energy region, and hence includes no noise. Therefore, the PC_X-ray image has a lower noise level and higher contrast level than the X-ray image obtained by the current integration mode. The PC_X-ray image also includes a contrast medium region in addition to the pixel region (to be referred to as the subject region hereinafter) associated with the subject P.

Note that the parameter assigned to each pixel of a PC_X-ray image is not limited to an integral value. For example, the image generator 67-2 may count the number of events for each detection element and assign the count to each pixel.

Upon executing step S4, the system controller 61-2 causes the positional shift calculation unit 69-2 to perform calculation processing for a positional shift index value (step S5). In step S5, the positional shift calculation unit 69-2 calculates the movement amount of a contrast medium region included in a PC_X-ray image to evaluate the positional shift amount of the subject at the time of a radiotherapy based on a radiotherapy plan. This movement amount is used as a positional shift index value. For example, a movement amount is defined by the distance between the reference points of contrast medium regions in the currently generated PC_X-ray image and a PC_X-ray image as a comparison target. A PC_X-ray image as a comparison target is a PC_X-ray image generated in the past, e.g., a PC_X-ray image generated immediately before the current PC_X-ray image or a PC_X-ray image generated by the first emission of radiotherapy X-rays. The reference point of a contrast medium region may be set to, for example, the center point, barycentric point, or end point of a contrast medium region. Note that a positional shift index value is not limited to the movement amount of a contrast medium region. For example, the number of pixels or the statistical value of the pixel values of the difference image based on the current PC_X-ray image and the past PC_X-ray image may be used as a positional shift index value. As a statistical value, a maximum value, average value, or the like may be used.

When calculating a positional shift index value, the apparatus may use a PC_X-ray image limited to a contrast medium instead of a PC_X-ray image associated with a subject. The apparatus generates a PC_X-ray image limited to a contrast medium in the following manner. First of all, the extraction unit 66-2 extracts the data associated with an energy region to which the K-absorption edge of the contrast medium belongs from the original acquired data. For example, an energy region to which the K-absorption edge of a contrast medium belongs may be set to the above window band centered on the energy value of the K-absorption edge of the contrast medium. The image generator 67-2 generates a PC_X-ray image limited to the contrast medium based on the acquired data associated with an energy region to which the K-absorption edge of the contrast medium belongs. The PC_X-ray image limited to the contrast medium includes only the contrast medium region. The positional shift calculation unit 69-2 can calculate a movement amount more accurately by using the PC_X-ray image limited to the contrast medium.

In addition, a positional shift index value is not limited to the distance (movement amount) between the reference points of contrast medium regions in the current PC_X-ray image and the past PC_X-ray image. A positional shift index value may be calculated by using only the current PC_X-ray image. For example, a positional shift index value may be defined by the distance from a fixed point in a PC_X-ray image to the reference point of a contrast medium region. A fixed point in a PC_X-ray image may be set to the center point, end point, or the like of the PC_X-ray image. In addition, as another positional shift index value, the ratios among a water region, bone region, and contrast medium region included in a PC_X-ray image may be used. The user may arbitrarily set a type of positional shift index value via the operation unit 64-2.

Upon executing step S5, the system controller 61-2 causes the determination unit 70-2 to perform determination processing (step S6). In step S6, the determination unit 70-2 determines whether the positional shift index value calculated in step S5 is less than a preset threshold. The user may arbitrarily set a value via the operation unit 64-2.

Upon determining that the positional shift index value is less than the threshold (YES in step S6), the system controller 61-2 determines whether the conditions for the termination of a radiotherapy are satisfied (step S7). The system controller 61-2 measures an administered dose or elapsed time from the start time of a radiotherapy. Upon determining that the measured administered dose, elapsed time, or the like does not exceed the threshold (NO in step S7), the system controller 61-2 causes the gantry controller 65-2 to continue a radiotherapy. The process then advances to step S2 to update the positional shift index value. The process returns to step S2 to cause the radiotherapy X-ray tube to emit radiotherapy X-rays again. The apparatus then repeats steps S2 to S7 in the same manner and repeatedly determines in step S6 whether an updated positional shift index value is less than a threshold. While the positional shift index value remains lower than the threshold, the apparatus repeats the loop of steps S2→S3→S4→S5→S6→S7→S2. Upon determining that the conditions for the termination of the radiotherapy (YES in step S7), the system controller 61-2 causes the gantry controller 65-2 to terminate the radiotherapy.

Upon determining that the positional shift index value is larger than the threshold before the conditions for the termination of the radiotherapy are satisfied (NO in step S6), the system controller 61-2 causes the gantry controller 65-2 to perform termination processing for the radiotherapy (step S8). In step S8, the gantry controller 65-2 controls the high voltage generator 17-2 to terminate the emission of radiotherapy X-rays. After the termination of the emission of radiotherapy X-rays, the apparatus keeps terminating the emission of X-rays unless the user issues a restart instruction via the operation unit 64-2.

Upon determining YES in step S7 or executing step S8, the system controller 61-2 terminates a radiotherapy.

With the function of automatically stopping a radiotherapy, the radiotherapy apparatus 100 can perform a radiotherapy limited to a radiotherapy irradiation region by stopping a radiotherapy immediately when the positional shift of the subject exceeds an allowable range. This improves the safety and accuracy of a radiotherapy. The radiotherapy apparatus 100 extracts non-noise acquired data from the acquired data obtained by the photon counting mode and calculates a positional shift index value by using a PC_X-ray image based on the non-noise acquired data. The PC_X-ray image according to this embodiment is lower in noise and higher in contrast than the X-ray image obtained in the current integration mode because various types of noise components are accurately removed. In contrast to this, the X-ray image obtained in the current integration mode includes many noise components because circuit noise cannot be removed. As a consequence, a positional shift index value according to this embodiment is higher in accuracy than that obtained in the current integration mode.

An application of the radiotherapy apparatus 100 according to the second embodiment will be described next. Note that the same reference numerals in the following description denote constituent elements having almost the same functions and arrangements in this embodiment, and a repetitive description will be made only when required.

[Application 1]

The radiotherapy apparatus 100 automatically stops a radiotherapy when the positional shift of a subject exceeds an allowable range. The radiotherapy apparatus 100 according to Application 1 automatically switches on and off radiotherapy X-rays in accordance with the motion of a subject, typically the motion of a contrast medium region.

Figure 18A:
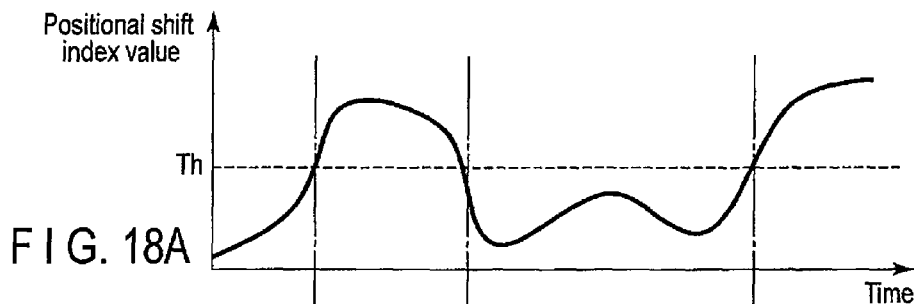
FIGS. 18A and 18B are timing charts associated with the emission of radiotherapy X-rays according to Application 1 of the second embodiment.
Figure 18B:
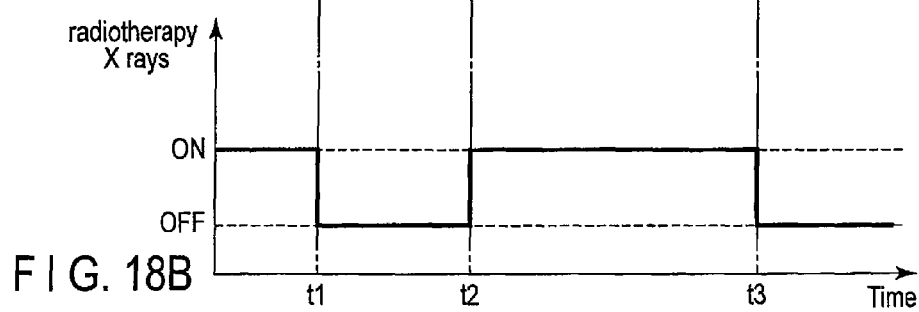

FIG. 18A and FIG. 18B show the timing chart associated with the emission of radiotherapy X-rays according to Application 1. FIG. 18A indicates temporal changes in positional shift index value calculated by the positional shift calculation unit 69-2. FIG. 18B indicates the ON/OFF switching timings of radiotherapy X-rays. As indicated by FIG. 18A, a positional shift index value becomes larger or smaller than a threshold Th due to the body motion of a subject. The determination unit 70-2 monitors a positional shift index value in real time and detects a timing at which the index value becomes larger than threshold Th and a timing at which the index value becomes smaller than the threshold Th. When the positional shift index value becomes larger than the threshold Th, the gantry controller 65-2 controls the high voltage generator 17-2 to stop the emission of radiotherapy X-rays. When the positional shift index value becomes smaller than the threshold Th, the gantry controller 65-2 controls the high voltage generator 17-2 to start the emission of radiotherapy X-rays.

As described above, the radiotherapy apparatus 100 according to Application 1 can automatically switch on and off radiotherapy X-rays in accordance with the motion of a subject. Therefore, when the positional shift returns to the allowable range, the apparatus can restart a radiotherapy without any instruction from the user. This reduces the user's labor associated with a radiotherapy and shortens the radiotherapy time.

[Application 1]

The radiotherapy apparatus 100 generates a PC_X-ray image mainly in the observation X-ray irradiation system. The radiotherapy apparatus 100 according to Application 2 causes not only the observation X-ray irradiation system but also the radiotherapy X-ray irradiation system to generate PC_X-ray images. A radiotherapy region during a radiotherapy is monitored by using the PC_X-ray images obtained by the two X-ray irradiation systems.

When both the X-ray irradiation systems simultaneously emit and detect X-ray photons, the data acquisition unit 20-2 receives electrical pulses from the radiotherapy detector 13-2 and the observation detector 15-2. The extraction unit 66-2 can discriminate events originating from radiotherapy X-rays from events originating from observation X-rays by using the large difference between radiotherapy X-ray energy and observation X-ray energy. The extraction unit 66-2 extracts the data associated with non-noise energy region from acquired data originating from the radiotherapy detector 13-2 and extracts the data associated with a non-noise energy region from acquired data originating from the observation detector 15-2 by using an energy threshold which can discriminate events from radiotherapy X-rays from events originating from observation X-rays. The image generator 67-2 generates PC_X-ray image data based on acquired data after extraction which originates from the radiotherapy detector 13-2. The image generator 67-2 generates PC_X-ray image data based on the acquired data after extraction which originates from the observation detector 15-2.

The PC_X-ray image associated with radiotherapy X-rays and the PC_X-ray image associated with observation X-rays are displayed side by side on the display unit 63-2. This allows the user to simultaneously observe the motion of a radiotherapy region such as an organ with the PC_X-ray image associated with the radiotherapy X-ray irradiation system and the PC_X-ray image associated with the observation X-ray irradiation system in real time while executing a radiotherapy. Therefore, the radiotherapy apparatus 100 according to Application 2 can improve the accuracy of a radiotherapy.

[Application 3]

As described in Application 2, the apparatus sometimes simultaneously emit radiotherapy X-rays and observation X-rays to observe a radiotherapy irradiation field during a radiotherapy. The interaction between different X-rays perpendicular to each other generates many scattered rays. Scattered rays reduce image quality and also reduce the primary ray counting performance of a photon counting type data acquisition system. The radiotherapy apparatus 100 according to Application 3 includes the post-collimators 21-2 and 25-2 having unique structures to reduce the number of scattered rays entering the X-ray detectors 13-2 and 15-2. The collimators according to Application 3 will be described below. Note that the post-collimators 21-2 and 25-2 according to Application 3 may be respectively mounted on the radiotherapy detector 13-2 and the observation detector 15-2 or may be mounted on one of them. Assume however that the post-collimator 21-2 mounted on the radiotherapy detector 13-2 has the same structure as that of the post-collimator 25-2 mounted on the observation detector 15-2.

Figure 19:
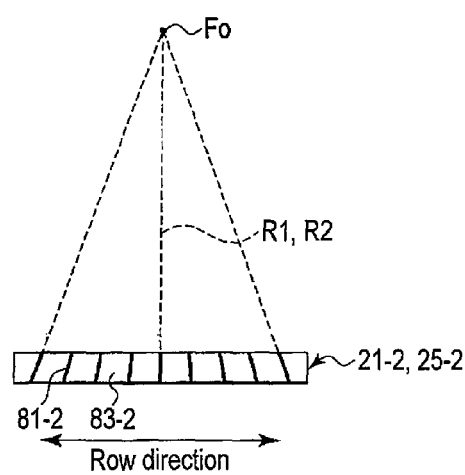
FIG. 19 is a view schematically showing the structure of a post-collimator associated with the channel direction according to Application 3 of the second embodiment.
Figure 20:
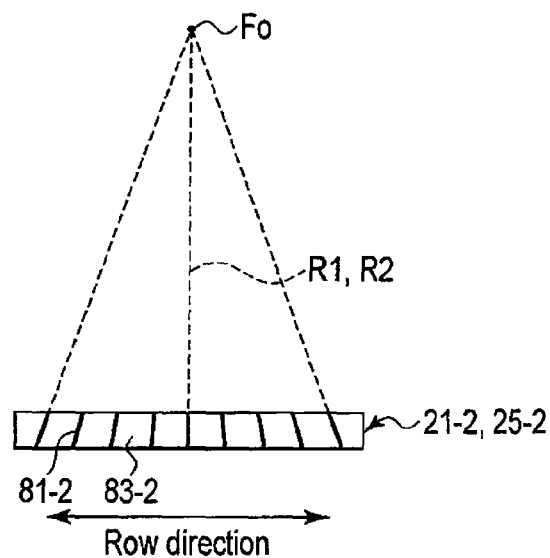
FIG. 20 is a view schematically showing the structure of a post-collimator associated with the row direction according to Application 3 of the second embodiment.
Figure 21:
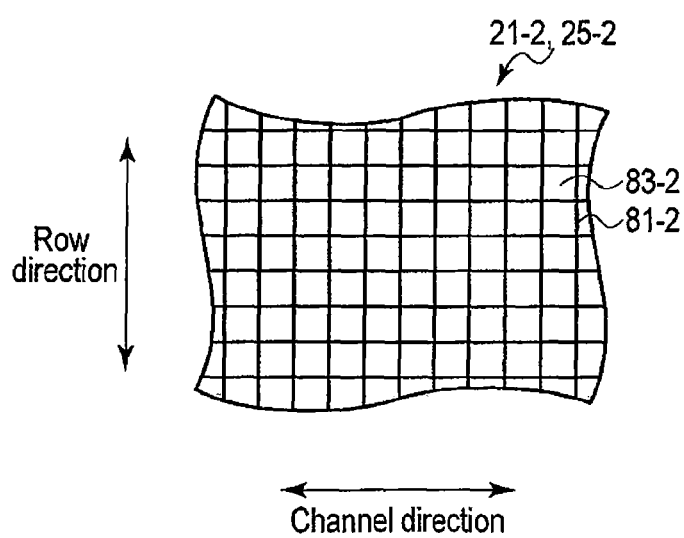
FIG. 21 is a plan view of a post-collimator according to Application 3 of the second embodiment.

FIG. 19 is a view schematically showing the structure of the post-collimators 21-2 and 25-2 associated with the channel direction. FIG. 20 is a view schematically showing the structure of the post-collimators 21-2 and 25-2 associated with the row direction. FIG. 21 is a plan view of the post-collimators 21-2 and 25-2. As shown in FIGS. 19, 20, and 21, the post-collimators 21-2 and 25-2 each have X-ray shielding plates 81-2 assembled into a lattice form in both the channel direction and the row direction. The X-ray shielding plate 81-2 is formed by using, as a material, a metal having an X-ray shielding property, e.g., aluminum, molybdenum, or tungsten. X-rays pass through openings 83-2 surrounded by the X-ray shielding plates 81-2 and reach the detection elements.

The X-ray shielding plates 81-2 are radially arrayed about an X-ray focus Fo. This makes all the openings 83-2 aim at the X-ray focus Fo and makes the X-ray shielding plates 81-2 become parallel to rays entering the openings 83-2. That is, the angles defined by the X-ray shielding plates 81-2 and axes R1 and R2 increase with increases in distance from the axes R1 and R2 in the channel and row directions. Arraying such X-ray shielding plates 81-2 can greatly reduce scattered rays entering the respective detection elements.

The post-collimators 21-2 and 25-2 according to Application 3 each have an incident structure which can reduce the interacting influence between X-rays even if radiotherapy X-rays and observation X-rays are simultaneously emitted. This improves the S/N ratio. In addition, the post-collimators 21-2 and 25-2 reduce scattered ray incidence events, and hence can improve the primary ray incidence event counting performance of the data acquisition unit 20-2.

Note the post-collimators 21-2 and 25-2 may be constituted by X-ray shielding plates arrayed along one of the channel and row directions.

[Application 4]

As described above, the radiotherapy apparatus 100 can reconstruct a three-dimensional PC_CT image (volume data) in a radiotherapy irradiation field by acquiring data using the observation X-ray irradiation system while rotating the rotating frame 11-2. However, the rotational speed of the rotating frame 11-2 of the radiotherapy gantry 10-2 is about 1 rmp, which is lower than the rotational speed of the rotating frame of the X-ray CT apparatus, and needs a long data acquisition time. Therefore, the body motion, rotation, and the like of a subject tend to degrade image quality. A radiotherapy apparatus 200 according to Application 4 generates a tomosynthesis image (volume data) by acquiring data while simultaneously moving the radiotherapy X-ray tube 12-2 and the radiotherapy detector 13-2 in accordance with the principle of tomosynthesis imaging. The radiotherapy apparatus 200 according Application 4 will be described below.

Figure 22:
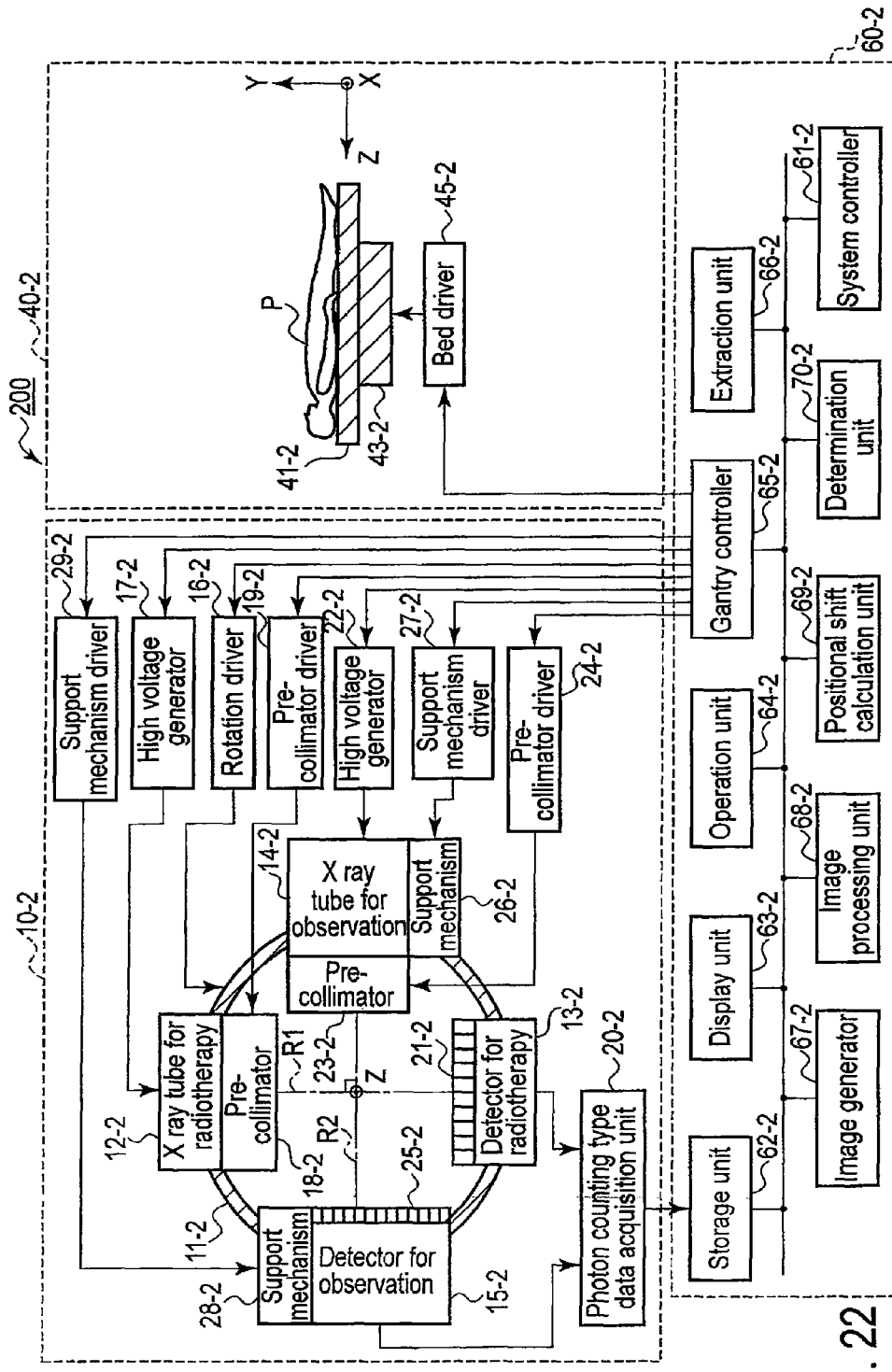
FIG. 22 is a block diagram showing the arrangement of a radiotherapy apparatus according to Application 4 of the second embodiment.

FIG. 22 is a block diagram of the radiotherapy apparatus 200 according to Application 4. As shown in FIG. 22, the radiotherapy gantry 10-2 includes an observation X-ray tube support mechanism 26-2, an observation X-ray tube support mechanism driver 27-2, an observation detector support mechanism 28-2, and an observation detector support mechanism driver 29-2. The support mechanism 26-2 is mounted on the rotating frame 11-2. The support mechanism 26-2 supports the observation X-ray tube 14-2 so as to allow it to rotate and move along a predetermined circumferential orbit (X-ray tube rotation orbit). The support mechanism driver 27-2 moves the observation X-ray tube 14-2 along an X-ray tube rotation orbit in accordance with a control signal from the gantry controller 65-2. The support mechanism 28-2 is mounted on the rotating frame 11-2. The support mechanism 28-2 supports the observation detector 15-2 so as to allow it to rotate and move along a predetermined circumferential orbit (X-ray detector rotation orbit). The support mechanism driver 29-2 moves the observation detector 15-2 along an X-ray detector rotation orbit in accordance with a control signal from the gantry controller 65-2. The gantry controller 65-2 synchronously controls the support mechanism driver 27-2 and the support mechanism driver 29-2 so as to synchronously move the observation X-ray tube 14-2 and the observation detector 15-2 to perform tomosynthesis imaging.

FIG. 23 is a view for explaining synchronous movement of the observation X-ray tube 14-2 and observation detector 15-2 in tomosynthesis imaging performed under the control of the gantry controller 65-2 according to Application 4. In this case, a rotation center axis RA is defined, which is perpendicular to an axis R1 connecting the X-ray focus of the radiotherapy X-ray tube 12-2 to the detection surface center of the radiotherapy detector 13-2. In the normal X-ray imaging mode, an axis R2 connecting the X-ray focus of the observation X-ray tube 14-2 to the detection surface center of the observation detector 15-2 coincides with the rotation center axis RA. The center point of an X-ray tube rotation orbit OT and an X-ray detector rotation orbit OD are located on the rotation center axis RA.

When performing tomosynthesis imaging, the apparatus moves the observation X-ray tube 14-2 around the rotation center axis RA along the X-ray tube rotation orbit OT, and moves the observation detector around the rotation center axis RA along the X-ray detector rotation orbit OD in synchronism with the movement of the observation X-ray tube 14-2. In this case, an intersection point IP between the axes R1 and R2 is spatially fixed. The relationship between the observation X-ray tube 14-2 and the observation detector 15-2 which face each other through the intersection point IP is maintained while the observation X-ray tube 14 and the observation detector 15 rotate and move.

The gantry controller 65-2 controls the high voltage generator 22-2 and the data acquisition unit 20-2 to perform X-ray imaging at a plurality of irradiation angles around the rotation center axis RA during the rotation of the observation X-ray tube 14-2 and observation detector 15-2. The image generator 67-2 reconstructs tomosynthesis image data (volume data) based on a plurality of PC_X-ray images respectively corresponding to a plurality of irradiation angles. As an image reconstruction method in tomosynthesis, for example, an existing tomosynthesis method such as a tomosynthesis method based on a shift addition method or FBP (filtered back projection) may be used.

As described above, according to Application 4, it is possible to prepare all the data required for image reconstruction of a tomosynthesis image as volume data without rotating the rotating frame 11-2. The radiotherapy apparatus 200 according to Application 4 can therefore generate volume data in real time even during a radiotherapy.

The positional shift calculation unit 69-2 in Application 4 may calculate a positional shift index value used for the automatic stop function for a radiotherapy according to this embodiment by using a tomosynthesis image. In this case, it is preferable to use, as a positional shift index value, registration information about anatomical reference regions in a tomosynthesis image and a radiotherapy plan CT image. More specifically, registration information is a distortion value/torsional value between reference regions based on a registration technique (deformable registration technique) with consideration to deformation. Reference regions include, for example, a contrast medium region, bone region, marker region, organ region, and radiotherapy region.

For example, the positional shift calculation unit 69-2 repeatedly calculates a distortion/torsional value between reference regions in each tomosynthesis image, which is repeatedly generated, and a radiotherapy planning CT image by using a deformable registration technique. If the calculated distortion/torsional value exceeds an allowable range, the gantry controller 65-2 controls the high voltage generator 17-2 to stop the emission of radiotherapy X-rays. If, for example, the distortion/torsional value exceeds an allowable dose distribution or DVH (dose value histogram), the gantry controller 65-2 controls the high voltage generator 17-2 to stop the emission of radiotherapy X-rays.

The second embodiment therefore improves positional shift detection accuracy, which in turn improves the accuracy of a radiotherapy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiotherapy system comprising:
   a first radiation source configured to generate radiation for observation;
   a first detector configured to detect radiation generated from the first radiation source and transmitted through a subject;
   a second radiation source configured to generate radiation for radiotherapy;
   a counting processing unit configured to generate first counting data, the first counting data including count value of photons included in a preset energy range based on a first output signal from the first detector; and
   an image generating unit configured to generate first medical image data based on the first counting data, wherein
   the counting processing unit comprises
   a data acquisition unit configured to acquire the first output signal from the first detector in a photon counting mode and generate first acquired data based on the first output signal, and
   an extraction unit configured to extract first counting data with a reduced noise component from the first acquired data by using a threshold set to an energy value corresponding to a window band which has an incident X-ray peak energy at its center and an energy width corresponding to an energy resolution, the reduced noise component being of an energy region lower than the threshold.

2. The radiotherapy system of claim 1, further comprising an index value counting unit configured to calculate an index value associated with a body motion amount of a subject by using the first medical image data.

3. The radiotherapy system of claim 2, further comprising:
a determination unit configured to determine whether the index value is not more than a threshold; and
a controller configured to stop emission of radiation from the second radiation source when it is determined that the index value is not less than the threshold.

4. The radiotherapy system of claim 2, further comprising:
a detection unit configured to detect a timing at which the index value becomes larger than a threshold and a timing at which the index value becomes smaller than the threshold; and
a controller configured to stop emission of radiation from the second radiation source when the index value becomes larger than the threshold and emit radiation from the second radiation source when the index value becomes smaller than the threshold.

5. The radiotherapy system of claim 1, wherein counting data associated with an incidence event of scattered rays of radiation from the second radiation source is removed from the first counting data.

6. The radiotherapy system of claim 1, further comprising:
a second detector configured to detect radiation generated from the second radiation source and transmitted through the subject; and
a support mechanism configured to support the first radiation source, the first detector, the second radiation source, and the second detector so as to make the first radiation source, the first detector, the second radiation source, and the second detector rotate about the same rotation axis such that the first radiation source and the first detector face each other through the subject, and the second radiation source and the second detector face each other through the subject.

7. The radiotherapy system of claim 6, wherein the counting processing unit generates second counting data included in preset another energy range based on a second output signal from the second detector.

8. The radiotherapy system of claim 7, wherein the image generating unit generates data of a second medical image based on the second counting data.

9. The radiotherapy system of claim 8, further comprising a display unit configured to display the first medical image and the second medical image side by side.

10. The radiotherapy system of claim 1, further comprising a post-collimator mounted on the first detector,
wherein the post-collimator includes X-ray shielding plates configured to remove scattered rays and radially arrayed about an X-ray focus of the first radiation source.

11. The radiotherapy system of claim 1, further comprising a support mechanism configured to support the first radiation source, the first detector, and the second radiation source so as to make the first radiation source and the first detector face each other through the subject.

12. The radiotherapy system of claim 1, further comprising:
a first support mechanism configured to support the first radiation source so as to allow the first radiation source to move along a first circumferential orbit centered on a predetermined axis;
a second support mechanism configured to support the first detector so as to allow the first detector to move along a second circumferential orbit centered on the predetermined axis; and
a controller configured to synchronously control the first support mechanism and the second support mechanism to move the first radiation source along the first circumferential orbit and move the first detector along the second circumferential orbit and to perform X-ray imaging at a plurality of radiation angles around the predetermined axis during movement of the first radiation source so as to perform tomosynthesis imaging,
wherein the image generating unit reconstructs tomosynthesis image data associated with the subject based on a plurality of medical images corresponding to the plurality of irradiation angles.

13. A radiotherapy system comprising:
an X-ray generator configured to generate X-ray photons;
an X-ray detection unit configured to detect X-ray photons generated from the X-ray generator and transmitted through a subject in a photon counting mode;
an extraction unit configured to extract specific output data associated with X-ray photons belonging to a specific energy region from output data from the X-ray detection unit by using a threshold preset for the specific energy region;
a reconstruction unit configured to reconstruct CT image data expressing a spatial distribution of CT values of a substance corresponding to the specific energy region based on the specific output data; and
a radiotherapy planning unit configured to decide a radiotherapy parameter associated with a radiotherapy for the subject by using the CT image data, wherein
the extraction unit is configured to extract the specific output data with a reduced noise component from output data from the X-ray detection unit by using a threshold set to an energy value corresponding to a window band which has an incident X-ray peak energy at its center and an energy width corresponding to an energy resolution, the reduced noise component being of an energy region lower than the threshold.

14. The radiotherapy system of claim 13, wherein the specific energy region is set to an energy region to which primary X-rays of X-ray photons detected by the X-ray detection unit belong.

15. The radiotherapy system of claim 13, wherein the extraction unit extracts the specific output data from the output data by removing an energy component of noise originating from an electronic circuit mounted on the X-ray detection unit from the output data.

16. The radiotherapy system of claim 13, wherein the specific energy region is set to an energy region to which a K-absorption edge of a specific substance existing in the subject out of X-ray photons detected by the X-ray detection unit belongs.

17. The radiotherapy system of claim 16, wherein the specific substance comprises at least one of a bone, a contrast agent, water, and another component.

18. The radiotherapy system of claim 17, further comprising an image processing unit, wherein the extraction unit extracts bone data associated with an energy region to which a K-absorption edge of the bone as the specific output data belongs from the output data, the reconstruction unit reconstructs, as the CT image, bone image data expressing a spatial distribution of CT values of the bone based on the bone data, and the image processing unit calculates a spatial positional shift amount between the bone image and a CT image generated immediately before the radiotherapy.

19. The radiotherapy system of claim 18, further comprising:
a radiation source configured to generate radiation;
a support body configured to mount the radiation source thereon;
a rotation support mechanism configured to support the support body so as to allow the support body to rotate;
a first driver configured to generate power for driving the rotation support mechanism;
a top configured to place the subject thereon;
a top support mechanism configured to support the top so as to allow the top to freely move;
a second driver configured to generate power for driving the top support mechanism; and
a controller configured to control the first driver and the second driver to move the top and the support body in accordance with the positional shift amount and to match a spatial position of the subject at the time of imaging of the CT image immediately before the radiotherapy with a spatial position of the subject at the time of imaging of the bone image.

20. A radiotherapy system comprising:
a first radiation source configured to generate radiation having a first energy;
a first detector configured to detect radiation generated from the first radiation source and transmitted through a subject;
a second radiation source configured to generate radiotherapy radiation having a second energy larger than the first energy;
a second detector configured to detect radiation generated from the second radiation source and transmitted through the subject;
a rotation support mechanism configured to support the first radiation source, the first detector, the second radiation source, and the second detector so as to make the first radiation source, the first detector, the second radiation source, and the second detector rotate about the same rotation axis such that the first radiation source and the first detector face each other through the subject, and the second radiation source and the second detector face each other through the subject;
a counting processing unit configured to obtain counting data included in a preset energy range based on a first output signal from the first detector;
an image generating unit configured to generate data of a medical image associated with the subject based on the counting data; and
a calculation unit configured to calculate an index value associated with a body motion amount of the subject by using the medical image, wherein
the counting processing unit comprises
a data acquisition unit configured to acquire the first output signal from the first detector in a photon counting mode and generate first acquired data based on the first output signal, and
an extraction unit configured to extract first counting data with a reduced noise component from the first acquired data by using a threshold set to an energy value corresponding to a window band which has an incident X-ray peak energy at its center and an energy width corresponding to an energy resolution, the reduced noise component being of an energy region lower than the threshold.

21. The radiotherapy system of claim 1, wherein the extraction unit is configured to set the threshold to a lower limit of the window band.

22. The radiotherapy system of claim 1, wherein the extraction unit is configured to determine the threshold based on an energy resolution of the first detector, flux of incident X-rays, and an energy distribution of incident X-rays.

* * * * *

UNITED STATES PATENT AND TRADEMARK OFFICE
CERTIFICATE OF CORRECTION

PATENT NO.        : 9,216,302 B2
APPLICATION NO.   : 13/967848
DATED             : December 22, 2015
INVENTOR(S)       : Takayuki Kuwahara et al.

It is certified that error appears in the above-identified patent and that said Letters Patent is hereby corrected as shown below:

On the title page, Item (73), the Assignees' Information is incorrect. Item (73) should read:

--(73)   Assignees:   KABUSHIKI KAISHA TOSHIBA, Minato-ku (JP); Toshiba Medical Systems Corporation, Otawara-shi (JP)--

Signed and Sealed this
Fifth Day of April, 2016

Michelle K. Lee
*Director of the United States Patent and Trademark Office*